US012281164B2

(12) United States Patent
Wang et al.

(10) Patent No.: US 12,281,164 B2
(45) Date of Patent: Apr. 22, 2025

(54) GENETICALLY ENGINEERED DUAL-TARGETING CHIMERIC ANTIGEN RECEPTOR AND USE THEREOF

(71) Applicant: WEST CHINA HOSPITAL, SICHUAN UNIVERSITY, Sichuan (CN)

(72) Inventors: Yongsheng Wang, Sichuan (CN); Qizhi Ma, Sichuan (CN); Dan Li, Sichuan (CN); Qiyu Yang, Sichuan (CN)

(73) Assignee: WEST CHINA HOSPITAL, SICHUAN UNIVERSITY, Sichuan (CN)

( * ) Notice: Subject to any disclaimer, the term of this patent is extended or adjusted under 35 U.S.C. 154(b) by 917 days.

(21) Appl. No.: 17/442,720

(22) PCT Filed: Nov. 12, 2019

(86) PCT No.: PCT/CN2019/117601
§ 371 (c)(1),
(2) Date: Sep. 24, 2021

(87) PCT Pub. No.: WO2020/125277
PCT Pub. Date: Jun. 25, 2020

(65) Prior Publication Data
US 2022/0185893 A1 Jun. 16, 2022

(30) Foreign Application Priority Data
Dec. 20, 2018 (CN) .......................... 201811567513.5

(51) Int. Cl.
| | |
|---|---|
| C07K 16/00 | (2006.01) |
| A61P 35/04 | (2006.01) |
| C07K 16/28 | (2006.01) |
| C07K 16/30 | (2006.01) |
| C07K 16/32 | (2006.01) |
| A61K 39/00 | (2006.01) |

(52) U.S. Cl.
CPC .......... C07K 16/2827 (2013.01); A61P 35/04 (2018.01); C07K 16/2863 (2013.01); C07K 16/30 (2013.01); C07K 16/32 (2013.01); A61K 2039/507 (2013.01); C07K 2317/622 (2013.01); C07K 2319/02 (2013.01); C07K 2319/03 (2013.01); C07K 2319/33 (2013.01); C07K 2319/50 (2013.01)

(58) Field of Classification Search
CPC ............ C07K 16/2827; C07K 16/2863; C07K 16/30; C07K 16/32; C07K 2317/622; C07K 2319/02; C07K 2319/03; C07K 2319/33
See application file for complete search history.

(56) References Cited

U.S. PATENT DOCUMENTS

| | | | |
|---|---|---|---|
| 10,934,363 B2 | 3/2021 | Fan et al. | |
| 2018/0327470 A1 | 11/2018 | Li et al. | |
| 2020/0038443 A1* | 2/2020 | Zhang | .................... A61K 35/17 |
| 2021/0060067 A1* | 3/2021 | Kim | .................... C12N 15/113 |

FOREIGN PATENT DOCUMENTS

| | | | |
|---|---|---|---|
| CN | 105384825 A | | 3/2016 |
| CN | 107325185 | * | 11/2017 |
| CN | 109485732 A | | 3/2019 |
| CN | 107325185 B | | 9/2019 |
| WO | 2017075440 A1 | | 5/2017 |
| WO | 2017080377 A1 | | 5/2017 |

OTHER PUBLICATIONS

John et al. (2013). Blockade of PD-1 immunosuppression boosts CAR T-cell therapy. Oncoimmunology, 2(10), e26286-1-e26286-3.
Meder et al. (2018). Combined VEGF and PD-L1 blockade displays synergistic treatment effects in an autochthonous mouse model of small cell lung cancer. Cancer research, 78(15), 4270-4281.
Zhang et al. (2018). Experimental study on bi-chimeric antigen receptors modified T lymphocytes targeting on acute myeloid leukemia. Journal of International Oncology, 385-390.
English language abstract for CN 109485732 A (2019).
International Search Report from corresponding PCT/CN2019/117601 mailed Feb. 6, 2020.

* cited by examiner

Primary Examiner — Lei Yao
(74) Attorney, Agent, or Firm — Caesar Rivise, PC

(57) ABSTRACT

The present invention belongs to the field of genetic engineering, and particularly relates to a genetically engineered dual-targeting chimeric antigen receptor. The present invention provides a genetically engineered dual-targeting chimeric antigen receptor and a host cell thereof in response to up-regulated expression of PD-L1 in tumor cells and immune cells after these cells are exposed to malignant serosal cavity effusion. The dual-targeting chimeric antigen receptor provided by the present invention competitively binds to PD-L1 to transform an inhibition signal of PD-L1 into an activation signal and to enhance the killing activity of T cells; meanwhile, 4-1BB introduced downstream thereof can promote proliferation and survival of T cells. In addition, the present invention also discloses a host cell expressing the above dual-targeting antigen receptor and a use thereof in preventing or treating solid tumors.

13 Claims, 4 Drawing Sheets
Specification includes a Sequence Listing.

(SEQ ID NO: 19)

Expression of PE/CAR molecules

T cells of different types co-cultured with target cells for 24h

GENETICALLY ENGINEERED DUAL-TARGETING CHIMERIC ANTIGEN RECEPTOR AND USE THEREOF

CROSS-REFERENCE TO RELATED APPLICATIONS

This application is a U.S. National Phase Application of PCT/CN2019/117601, filed Nov. 12, 2019, which claims priority to CN 201811567513.5, filed Dec. 20, 2018, the contents of which applications are incorporated herein by reference in their entireties for all purposes.

SEQUENCE LISTING STATEMENT

Incorporated herein by reference in its entirety is a Sequence Listing named "C127820061_SequenceListing", which is being submitted to the USPTO via EFS-web on even date herewith as an ASCII text file 31 KB in size. This file, which was created on Sep. 24, 2021, constitutes both the paper and computer readable form of the Sequence Listing.

FIELD OF THE INVENTION

The present invention belongs to the field of genetic engineering, particularly relates to a genetically engineered dual-targeting chimeric antigen receptor, an immunoreactive cell expressing the chimeric antigen receptor, and a use of the chimeric antigen receptor and the immunoreactive cell in preparing drugs for preventing and treating serosal cavity metastasis of malignant tumors.

BACKGROUND OF THE INVENTION

In 2013, immunotherapy for tumors headed the list of Top 10 Scientific and Technological Advances of the Year in *Science*, among which CAR-T therapy, CTLA-4 and PD-1/PD-L1 antibody therapy were considered as the three major advances in tumor immunotherapy. Chimeric antigen receptor (CAR) T cells (CAR-Ts) constructed by using antigen antibody scFv fragments in combination with intracellular activation and proliferation signals of T cells enable T cells to directly acquire antibody-specific recognition ability and become effector T cells independent of human leukocyte antigen (HLA) restriction. The killing activity of acquired CAR-Ts mainly depends on recognition of antigens by single chain receptors on surfaces of the CAR-Ts with specific killing activity. Clinical studies have confirmed that such CAR-Ts are able to amplify in vivo, survive for a long time and develop immunological memory, and exhibit efficient anti-tumor activity even for refractory hematologic tumors. Unfortunately, CAR-Ts are facing challenges in the treatment of solid tumors, and have made slow progress in clinical applications so far.

There are several challenges when CAR-Ts are used for systemic treatment of solid tumors: (1) most of therapeutic targets for solid tumors are tumor-associated antigens (TAAs). Since TAAs are expressed in normal tissues, potential toxicity is presented when targeting TAAs, and "on-target, off-tumor" toxicity is observed in clinical treatment with CAR-Ts targeting Her2, MART1 and CAIX, suggesting that systemic CAR-T treatment for TAAs needs to be designed carefully; (2) for solid tumors treated with CAR-Ts, entry of CAR-Ts into solid tumors through blood vessels is an important step to exert therapeutic effects, but it is difficult for CAR-Ts to pass through basement membrane of blood vessels, which affects the therapeutic effect; and (3) the interior of solid tumors is an immunosuppressive microenvironment in which TGF-β can be secreted, PD-1/PD-L1 inhibitory signals can be activated, and the activity of effector cells can be suppressed through immunosuppressive cells such as MDSC and Treg. It is clear that there are many difficulties in using CAR-Ts for systemic CAR-T therapy.

It is believed that the use of CAR-Ts for local treatment of solid tumors can evade the above challenges and play a positive role in treating the specific conditions of patients with specific solid tumors. In the study, CAR-Ts are intended for serosal cavity infusion to prevent and treat serosal cavity metastasis of malignant tumors, so as to investigate the anti-tumor effect and immune mechanism of CAR-Ts in the serosal cavity.

Malignant tumors such as lung cancer, colon cancer, ovarian cancer, breast cancer, gastric cancer and lymphoma are prone to cause serosal cavity metastasis in pleural cavity, peritoneal cavity and pericardial cavity, often leading to effusions in pleural cavity and peritoneal cavity or further complication with malignant serosal effusion. It is difficult for tumor patients with metastasis in pleural and peritoneal cavities complicated with pleural or peritoneal effusion to tolerate systemic treatment. Even if the patients are clinically treated by drainage and infusion chemotherapy, the efficacy is still limited. Complications such as dyspnea and intestinal obstruction seriously affect the physiological functions and quality of life of patients, and the median survival time is often only 3-6 months. In addition, some tumor patients only show the manifestation of postoperative serosal cavity diffusion, such as peritoneal carcinomatosis (PC). Such patients are eligible to receive cytoreductive surgery and hyperthermic intraperitoneal chemotherapy to significantly prolong the survival rate. Unfortunately, however, even in patients who have received cytoreductive surgery and hyperthermic intraperitoneal chemotherapy, intraperitoneal recurrence occurs in approximately 80% of the patients within three years after treatment, due to inability to effectively remove tumor cells from the peritoneal cavity. Therefore, for such patients with serosal cavity metastasis, local treatment is the main treatment available, but has limited efficacy. Previous studies have shown that once tumor cells were exposed to malignant pleural/peritoneal effusion, epithelial-mesenchymal transition (EMT) could be induced, and produced high-frequency cancer stem cells (CSCs). Such cells highly expressed drug-resistant proteins such as ABCB1 and ABCG2, generating therapeutic resistance.

Studies have shown that CAR-Ts also had effective killing activity against CSCs. Some studies have been carried out to investigate local application of CAR-Ts; for example, local intrapleural infusion of MSLN CAR-T targeting Mesothelin in animal experiments had proved the effectiveness and safety of local application. Therefore, the use of CAR-Ts is expected to be an effective means to prevent and treat serosal cavity metastasis of malignant tumors, but research on application of CAR-Ts in serosal cavity environment is extremely limited worldwide.

Treatment with CAR-Ts through serosal cavity infusion has two advantages. First, it is safe with low systemic toxicity. CAR-Ts having specific killing activity against tumor cells completely depend on targeted tumor antigens, also kill normal tissues expressing antigens. CAR-Ts exert killing effect in the serosal cavity, despite of massive proliferation, CAR-Ts are less likely to circulate in the blood in large quantities, and are easy to handle locally to eliminate potential toxicity. Second, therapeutic targets of CAR-Ts are extended, and more TAAs can be used as therapeutic targets. Since the serosal cavity is mainly surrounded by connective tissues, and expression profiles are quite different from those of epithelial-derived tumor cells, a large number of epithelial-derived antigens may become potential therapeutic targets. More importantly, the effect of CAR-Ts mainly depends on antigens but not on tumor sources, and thus CAR-Ts have broad-spectrum tumor-killing activity (killing activity against various tumors expressing the antigens), so that serosal cavity metastasis can be treated as a separate indication clinically.

In a serosal cavity environment, the PD-L1 expression up-regulated in tumor cells and immune cells to escape from immune attacks. It is found that blocking PD-1/PD-L1 signals can improve the efficacy of CAR-T treatment, but the clinical treatment is expensive, and tumor cells still exhibit a high expression of VEGFR1 or HER2 after treatment of malignant effusion.

In response to the challenge of up-regulated expression of PD-L1 in tumor cells and immune cells after exposing to serosal effusion, a dual-targeting CAR viral vector targeting both VEGFR1 (or HER2) and PD-L1 is designed and constructed based on previous work. In the present invention, dual-targeting CAR-Ts (dual CAT-Ts) of VEGFR1 (or HER2) and PD-L1 are taken as examples to illustrate that the dual-targeting chimeric antigen receptor containing a PD-L1 target can eliminate immune escape of tumor cells, relieve immunosuppression of immune cells and prevent and treat malignant tumors, and can be used for clinically relevant prevention and treatment.

SUMMARY OF THE INVENTION

The present invention provides a genetically engineered dual-targeting chimeric antigen receptor and a host cell thereof in response to the up-regulated expression of PD-L1 in tumor cells and immune cells after exposing to malignant serosal effusion.

The first technical problem to be solved by the present invention is to provide a genetically engineered dual-targeting chimeric antigen receptor that can bind two different targets and transmit two signals.

According to the genetically engineered dual-targeting chimeric antigen receptor provided by the present invention, the dual-targeting chimeric antigen receptor is formed by linking a chimeric antigen receptor 1 and a chimeric antigen receptor 2 capable of recognizing PD-L1 through a linker peptide.

In the genetically engineered dual-targeting chimeric antigen receptor, the chimeric antigen receptor 2 comprises a single-chain fragment variable (scFv) antibody of PD-L1, a transmembrane domain and an intracellular domain.

Further, the scFv antibody of PD-L1 refers to scFv antibody binding PD-L1 molecules on surfaces of tumor cells or immune cells.

Further, the transmembrane domain is a CD8 transmembrane domain.

Further, the intracellular domain is a 4-1BB intracellular domain.

The chimeric antigen receptor 2 is composed of a scFv antibody of human PD-L1, a CD8 transmembrane domain and a 4-1BB costimulatory molecular peptide fragment.

Specifically, an amino acid sequence of the chimeric antigen receptor 2 is shown in SEQ ID NO: 1:

DIQMTQSPSSLSASVGDRVTITCRASQDVSTAVAWYQQKPGKAPKLLIYS
ASFLYSGVPSRFSGSGSGTDFTLTISSLQPEDFATYYCQQYLYHPATFGQ

-continued

GTKVEIKGGGGSGGGGSGGGGSEVQLVESGGGLVQPGGSLRLSCAASGFT
FSDSWIHWVRQAPGKGLEWVAWISPYGGSTYYADSVKGRFTISADTSKNT
AYLQMNSLRAEDTAVYYCARRHWPGGFDYWGQGTLVTVSAAAAFVPVFLP
AKPTTTPAPRPPTPAPTIASQPLSLRPEACRPAAGGAVHTRGLDFACDIY
IWAPLAGTCGVLLLSLVITLYCNHRNRFSVVKRGRKKLLYIFKQPFMRPV
QTTQEEDGCSCRFPEEEEGGCEL.

Further, a coding nucleotide sequence of the chimeric antigen receptor 2 is shown in SEQ ID NO: 2:

GACATCCAAATGACCCAGAGCCCTAGCTCCCTGTCCGCTAGCGTGGGCGA
CAGGGTGACCATCACCTGCAGAGCCAGCCAGGACGTGAGCACCGCCGTGG
CCTGGTACCAGCAGAAGCCCGGCAAGGCCCCCAAGCTGCTGATCTACAGC
GCCTCCTTCCTGTACTCCGGCGTGCCCTCCAGATTTAGCGGCAGCGGCAG
CGGCACAGACTTCACCCTCACCATCAGCTCCCTGCAGCCTGAGGACTTCG
CCACATACTACTGCCAGCAGTACCTCTACCACCCTGCCACCTTCGGCCAA
GGCACCAAGGTGGAGATCAAGGGCGGCGGAGGTTCTGGCGGAGGCGGCTC
CGGAGGAGGAGGCAGCGAAGTGCAGCTGGTGGAGAGCGGAGGAGGACTGG
TGCAGCCTGGCGGAAGCCTGAGGCTGAGCTGTGCTGCCAGCGGCTTCACC
TTCTCCGACTCCTGGATTCATTGGGTCAGGCAGGCCCCCGGAAAAGGACT
GGAGTGGGTCGCCTGGATCTCCCCTTACGGCGGCAGCACCTACTACGCCG
ACAGCGTGAAGGGCAGGTTCACCATCAGCGCCGATACCAGCAAGAACACC
GCCTACCTGCAGATGAACTCCCTGAGGGCTGAGGACACCGCCGTGTACTA
CTGCGCCAGGAGGCACTGGCCTGGCGGATTCGACTACTGGGGCCAGGGCA
CCCTGGTGACCGTGTCCGCCGCCGCCGCCTTCGTGCCTGTGTTTCTGCCC
GCCAAGCCCACCACCACACCTGCTCCCAGACCTCCCACACCTGCCCCTAC
CATCGCTAGCCAGCCCCTGAGCCTGAGACCCGAGGCTTGTAGGCCTGCTG
CTGGCGGAGCCGTGCACACAAGAGGCCTGGACTTCGCCTGCGACATCTAC
ATCTGGGCCCCCCTGGCCGGAACATGTGGAGTGCTGCTGCTGAGCCTGGT
GATCACCCTGTACTGCAACCACAGGAACAGGTTCAGCGTGGTGAAGAGGG
GCAGGAAGAAGCTGCTGTACATCTTCAAGCAGCCCTTCATGAGGCCCGTG
CAGACCACCCAGGAGGAGGATGGCTGCAGCTGCAGGTTCCCTGAAGAGGA
GGAGGGCGGCTGCGAGCTGTGA.

The chimeric antigen receptor 1 comprises a scFv antibody capable of binding a tumor specific antigen or a tumor-associated antigen, a transmembrane domain and an intracellular immunoreceptor tyrosine-based activation motif.

The tumor specific antigen or the tumor-associated antigen is at least one of CD19, CD20, MUC1, EGFR, EGFRvIII, HER2, ERBB3, ERBB4, VEGFR1, VEGFR2, EpCAM, CD44 or IGFR.

The scFv antibody capable of binding a tumor specific antigen or a tumor-associated antigen is a scFv antibody capable of binding EGFR family proteins including EGFR, HER2, ERBB3, ERBB4 or EGFRvIII, VEGFR1, VEGFR2, EpCAM, CD19, CD20 and CD44. Preferably, the scFv antibody is VEGFR1 scFv antibody or HER2 scFv antibody.

The transmembrane domain is at least one of CD28, CD8, CD3ζ, CD134, CD137, ICOS, DAP10 or CD27 transmembrane domains. Preferably, the transmembrane domains of the chimeric antigen receptors 1 and 2 are selected from different transmembrane domains. More preferably, the transmembrane domain of the chimeric antigen receptor 1 is a CD28 transmembrane domain, and the transmembrane domain of the chimeric antigen receptor 2 is a CD8 transmembrane domain.

The intracellular immunoreceptor tyrosine-based activation motif comprises an immunoreceptor tyrosine-based activation motif signal chain selected from CD3ζ or FcεRI.

The chimeric antigen receptor 1 is composed of a signal peptide, a scFv antibody of human VEGFR1, a CD28 transmembrane domain and a CD3ζ binding domain.

An amino acid sequence of the signal peptide is shown in SEQ ID NO: 11:

MALPVTALLLPLALLLHAARP.

A nucleotide sequence of the signal peptide is shown in SEQ ID NO: 12:

ATGGCCTTACCAGTGACCGCCTTGCTCCTGCCGCTGGCCTTGCTGCTC

CACGCCGCCAGGCCG.

Further, an amino acid sequence of the chimeric antigen receptor 1 is shown in SEQ ID NO: 3:

MALPVTALLLPLALLLHAARPEIVLTQSPGTLSLSPGERATLSCRASQSV

SSSYLAWYQQKPGQAPRLLIYGASSRATGIPDRFSGSGSGTDFTLTISRL

EPEDFAVYYCQQYGSSPLTFGGGTKVEIKGGGSGGGGSGGGGSQAQVVE

SGGGVVQSGRSLRLSCAASGFAFSSYGMHWVRQAPGKGLEWVAVIWYDGS

NKYYADSVRGRFTISRDNSENTLYLQMNSLRAEDTAVYYCARDHYGSGVH

HYFYYGLDVWGQGTTVTVSSKIEVMYPPPYLDNEKSNGTIIHVKGKHLCP

SPLFPGPSKPFWVLVVVGGVLACYSLLVTVAFIIFWVRSKRSRLLHSDYM

NMTPRRPGPTRKHYQPYAPPRDFAAYRSAPAYQQGQNQLYNELNLGRREE

YDVLDKRRGRDPEMGGKPQRRKNPQEGLYNELQKDKMAEAYSEIGMKGER

RRGKGHDGLYQGLSTATKDTYDALHMQALPPR.

Further, a nucleotide sequence of the chimeric antigen receptor 1 is shown in SEQ ID NO: 4:

ATGGCCTTACCAGTGACCGCCTTGCTCCTGCCGCTGGCCTTGCTGCTCCA

CGCCGCCAGGCCGGAGATCGTGCTGACACAGAGCCCTGGCACCCTGAGCC

TGTCCCCCGGCGAAAGAGCCACCCTGTCCTGCAGAGCCAGCCAGAGCGTG

AGCAGCTCCTATCTGGCCTGGTACCAGCAGAAGCCTGGCCAGGCCCCCAG

ACTCCTGATCTACGGCGCCAGCAGCAGAGCCACCGGCATCCCCGATAGAT

TCAGCGGCTCCGGCAGCGGAACCGACTTTACCCTGACCATCTCCAGACTG

GAGCCCGAGGACTTTGCCGTGTACTACTGCCAGCAGTACGGCAGCAGCCC

CCTGACATTCGGCGGCGGCACAAAGGTGGAGATCAAAGGCGGCGGAGGTT

CTGGAGGAGGAGGAAGCGGAGGAGGAGGCAGCCAGGCTCAGGTGGTCGAA

AGCGGCGGAGGAGTGGTGCAGAGCGGAAGGTCCCTGAGGCTGAGCTGCGC

TGCTAGCGGCTTTGCCTTCTCCTCCTACGGCATGCACTGGGTGAGACAGG

CCCCTGGCAAGGGCCTGGAATGGGTGGCTGTGATCTGGTACGACGGCAGC

AACAAGTACTACGCCGACAGCGTGAGGGGCAGGTTCACCATCAGCAGGGA

CAACAGCGAAAACACCCTGTACCTGCAGATGAACAGCCTCAGGGCCGAGG

ATACCGCCGTGTATTATTGCGCCAGGGATCACTACGGAAGCGGCGTGCAC

CATTACTTCTATTACGGCCTGGACGTGTGGGGCCAGGGCACAACAGTGAC

CGTGTCCAGCAAAATTGAAGTTATGTATCCTCCTCCTTACCTAGACAATG

AGAAGAGCAATGGAACCATTATCCATGTGAAAGGGAAACACCTTTGTCCA

AGTCCCCTATTTCCCGGACCTTCTAAGCCCTTTTGGGTGCTGGTGGTGGT

TGGTGGAGTCCTGGCTTGCTATAGCTTGCTAGTAACAGTGGCCTTTATTA

TTTTCTGGGTGAGGAGTAAGAGGAGCAGGCTCCTGCACAGTGACTACATG

AACATGACTCCCCGCCGCCCCGGGCCCACCCGCAAGCATTACCAGCCCTA

TGCCCCACCACGCGACTTCGCAGCCTATCGCTCCGCCCCGCGTACCAGC

AGGGCCAGAACCAGCTCTATAACGAGCTCAATCTAGGACGAAGAGAGGAG

TACGATGTTTTGGACAAGAGACGTGGCCGGGACCCTGAGATGGGGGGAAA

GCCGCAGAGAAGGAAGAACCCTCAGGAAGGCCTGTACAATGAACTGCAGA

AAGATAAGATGGCGGAGGCCTACAGTGAGATTGGGATGAAAGGCGAGCGC

CGGAGGGGCAAGGGGCACGATGGCCTTTACCAGGGTCTCAGTACAGCCAC

CAAGGACACCTACGACGCCCTTCACATGCAGGCCCTGCCCCCTCGC.

On the other hand, the chimeric antigen receptor 1 is composed of a signal peptide, a scFv antibody of human HER2, a CD28 transmembrane domain and a CD3ζ binding domain.

An amino acid sequence of the signal peptide is shown in SEQ ID NO: 11.

A nucleotide sequence of the signal peptide is shown in SEQ ID NO: 12.

Further, an amino acid sequence of the chimeric antigen receptor 1 is shown in SEQ ID NO: 5:

MALPVTALLLPLALLLHAARPMQVQLQQSGPELKKPGETVKISCKASGYP

FTNYGMNWVKQAPGQGLKWMGWINTSTGESTFADDFKGRFDFSLETSANT

AYLQINNLKSEDSATYFCARWEVYHGYVPYWGQGTTVTVSSGGGGSGGGG

SGGGGSDIQLTQSHKFLSTSVGDRVSITCKASQDVYNAVAWYQQKPGQSP

KLLIYSASSRYTGVPSRFTGSGSGPDFTFTISSVQAEDLAVYFCQQHFRT

PFTFGSGTKLEIKKIEVMYPPPYLDNEKSNGTIIHVKGKHLCPSPLFPGP

SKPFWVLVVVGGVLACYSLLVTVAFIIFWVRSKRSRLLHSDYMNMTPRRP

GPTRKHYQPYAPPRDFAAYRS+APAYQQGQNQLYNELNLGRREEYDVLDK

RRGRDPEMGGKPQRRKNPQEGLYNELQKDKMAEAYSEIGMKGERRRGKGH

DGLYQGLSTATKDTYDALHMQALPPR.

Further, a coding nucleotide sequence of the chimeric antigen receptor 1 is shown in SEQ ID NO: 6:

```
ATGGCCTTACCAGTGACCGCCTTGCTCCTGCCGCTGGCCTTGCTGCTCCA
CGCCGCCAGGCCGATGCAGGTACAACTGCAGCAGTCAGGACCTGAACTGA
AGAAGCCTGGAGAGACAGTCAAGATCTCCTGCAAGGCCTCTGGGTATCCT
TTCACAAACTATGGAATGAACTGGGTGAAGCAGGCTCCAGGACAGGGTTT
AAAGTGGATGGGCTGGATTAACACCTCCACTGGAGAGTCAACATTTGCTG
ATGACTTCAAGGGACGGTTTGACTTCTCTTTGGAAACCTCTGCCAACACT
GCCTATTTGCAGATCAACAACCTCAAAAGTGAAGACTCGGCTACATATTT
CTGTGCAAGATGGGAGGTTTACCACGGCTACGTTCCTTACTGGGGCCAAG
GGACCACGGTCACCGTTTCCTCTGGCGGTGGCGGTTCTGGTGGCGGTGGC
TCCGGCGGTGGCGGTTCTGACATCCAGCTGACCCAGTCTCACAAATTCCT
GTCCACTTCAGTAGGAGACAGGGTCAGCATCACCTGCAAGGCCAGTCAGG
ATGTGTATAATGCTGTTGCCTGGTATCAACAGAAACCAGGACAATCTCCT
AAACTTCTGATTTACTCGGCATCCTCCCGGTACACTGGAGTCCCTTCTCG
CTTCACTGGCAGTGGCTCTGGGCCGGATTTCACTTTCACCATCAGCAGTG
TGCAGGCTGAAGACCTGGCAGTTTATTTCTGTCAGCAACATTTTCGTACT
CCATTCACGTTCGGCTCGGGGACAAAATTGGAGATCAAAAAAATTGAAGT
TATGTATCCTCCTCCTTACCTAGACAATGAGAAGAGCAATGGAACCATTA
TCCATGTGAAAGGGAAACACCTTTGTCCAAGTCCCCTATTTCCCGGACCT
TCTAAGCCCTTTTGGGTGCTGGTGGTGGTTGGTGGAGTCCTGGCTTGCTA
TAGCTTGCTAGTAACAGTGGCCTTTATTATTTTCTGGGTGAGGAGTAAGA
GGAGCAGGCTCCTGCACAGTGACTACATGAACATGACTCCCCGCCGCCCC
GGGCCCACCCGCAAGCATTACCAGCCCTATGCCCCACCACGCGACTTCGC
AGCCTATCGCTCCGCCCCCGCGTACCAGCAGGGCCAGAACCAGCTCTATA
ACGAGCTCAATCTAGGACGAAGAGAGGAGTACGATGTTTTGGACAAGAGA
CGTGGCCGGGACCCTGAGATGGGGGGAAAGCCGCAGAGAAGGAAGAACCC
TCAGGAAGGCCTGTACAATGAACTGCAGAAAGATAAGATGGCGGAGGCCT
ACAGTGAGATTGGGATGAAAGGCGAGCGCCGGAGGGGCAAGGGGCACGAT
GGCCTTTACCAGGGTCTCAGTACAGCCACCAAGGACACCTACGACGCCCT
TCACATGCAGGCCCTGCCCCCTCGCTAA.
```

The linker peptide is at least one of Furin or P2A.

An amino acid sequence of the linker peptide P2A is shown in SEQ ID NO: 7, and a nucleotide sequence encoding the linker peptide P2A is shown in SEQ ID NO: 8. An amino acid sequence of the linker peptide Furin is shown in SEQ ID NO: 9, and a nucleotide sequence encoding the linker peptide Furin is shown in SEQ ID NO: 10.

An amino acid sequence of the linker peptide P2A is shown in SEQ ID NO: 7:

SGSGEGRGSLLTCGDVEENPGP.

A nucleotide sequence of the linker peptide P2A is shown in SEQ ID NO: 8:

AGCGGCAGCGGCGAGGGAAGAGGAAGCCTGCTGACCTGCGGCGATG
TGGAGGAGAATCCCGGCCCC.

An amino acid sequence of the linker peptide Furin is shown in SEQ ID NO: 9:

RRKR.

A nucleotide sequence of the linker peptide Furin is shown in SEQ ID NO 10:

AGGAGGAAGAGA.

The chimeric antigen receptor 1 and the chimeric antigen receptor 2 of the present invention are co-expressed by a vector.

The present invention also provides an expression vector for simultaneous expression of the chimeric antigen receptor 1 and the chimeric antigen receptor 2. Further, the expression vector is a eukaryotic or prokaryotic expression vector, and the eukaryotic expression vector is a plasmid; the prokaryotic expression vector is a viral vector including retrovirus, recombinant lentivirus and recombinant adenovirus; further, the viral vector is pWPXLd.

The present invention further provides a host cell containing the above expression vector. Preferably, the host cell is an immunoreactive cell, preferably a T cell, a monocyte, a natural killer cell or a neutrophil, and more preferably a T cell or a natural killer cell.

The present invention further provides a use of the dual-targeting chimeric antigen receptor, the recombinant vector containing the chimeric antigen receptor and the host cell containing the recombinant vector in preparing drugs for preventing or treating serosal cavity metastasis of malignant tumors.

Further, in the above use, the malignant tumor is a solid tumor, in particular at least one of lung cancer, hepatocellular carcinoma, colon cancer, rectal cancer, breast cancer, ovarian cancer, gastric cancer, cholangiocarcinoma, gallbladder cancer, esophageal cancer, renal cancer, pancreatic cancer or prostate cancer.

Compared with the prior the design of CAR-Ts, the present invention has the following advantageous effects:

By constructing a recombinant vector containing a dual-targeting chimeric antigen receptor expression unit in the present invention, two chimeric antigen receptors can be simultaneously expressed in a host cell, one chimeric antigen receptor is a receptor that binds a tumor specific antigen or a tumor-associated antigen and is capable of exerting specific targeting effects, and the other chimeric antigen receptor is a PD-L1 receptor that is capable of binding human PD-L1 antigen. When both chimeric antigen receptors are present in the host cell, the effect of simultaneous binding of dual targets can be achieved. The dual-targeting specific binding form in the method of the present invention can be utilized for preparing drugs for preventing and treating serosal cavity metastasis of malignant tumors, and provides a basis for preventing and treating serosal cavity metastasis of malignant tumors.

DETAILED DESCRIPTION OF THE PREFERRED EMBODIMENTS

Figure 1:
FIG. 1 is a schematic diagram showing the structure of the dual-targeting chimeric antigen receptor of the present invention (in which the variable region can be replaced by any scFv antibody fragment)

The present invention will be described in detail with reference to the preferred embodiments and accompanying drawings. In the following examples, where no specific experimental conditions indicated, they are in accordance with conventional conditions well known to those skilled in the art, such as conditions described in Sambrook J, Russell D. W., 2001, Molecular Cloning: A laboratory manual (3$^{rd}$ ed), Spring Harbor Laboratory Press, or conditions suggested by manufacturers.

Example 1 Construction of Recombinant Lentiviral Vector for Dual-Targeting Chimeric Antigen Receptor A recombinant vector for a dual-targeting chimeric antigen receptor was constructed with the following expression framework: HER2 scFv antibody-CD28 transmembrane domain-CD3ζ-Furin-P2A-PD-L1 scFv antibody-CD8 transmembrane domain-4-1BB from 5' to 3'.

An amino acid sequence of a signal peptide of HER2 is shown in SEQ ID NO: 11, and a nucleotide sequence of the signal peptide of HER2 is shown in SEQ ID NO: 12.

An amino acid sequence of HER2scFv antibody is shown in SEQ ID NO: 13:

MQVQLQQSGPELKKPGETVKISCKASGYPFTNYGMNWVKQAPGQGLK

WMGWINTSTGESTFADDFKGRFDFSLETSANTAYLQINNLKSEDSAT

YFCARWEVYHGYVPYWGQGTTVTVSSGGGGSGGGGSGGGGSDIQLTQ

SHKFLSTSVGDRVSITCKASQDVYNAVAWYQQKPGQSPKLLIYSASS

RYTGVPSRFTGSGSGPDFTFTISSVQAEDLAVYFCQQHFRTPFTFGS

GTKLEIK.

A coding nucleotide sequence of HER2 scFv antibody is shown in SEQ ID NO: 14:

ATGCAGGTACAACTGCAGCAGTCAGGACCTGAACTGAAGAAGCCTGGAGA

GACAGTCAAGATCTCCTGCAAGGCCTCTGGGTATCCTTTCACAAACTATG

GAATGAACTGGGTGAAGCAGGCTCCAGGACAGGGTTTAAAGTGGATGGGC

TGGATTAACACCTCCACTGGAGAGTCAACATTTGCTGATGACTTCAAGGG

ACGGTTTGACTTCTCTTTGGAAACCTCTGCCAACACTGCCTATTTGCAGA

TCAACAACCTCAAAAGTGAAGACTCGGCTACATATTTCTGTGCAAGATGG

GAGGTTTACCACGGCTACGTTCCTTACTGGGGCCAAGGGACCACGGTCAC

CGTTTCCTCTGGCGGTGGCGGTTCTGGTGGCGGTGGCTCCGGCGGTGGCG

GTTCTGACATCCAGCTGACCCAGTCTCACAAATTCCTGTCCACTTCAGTA

GGAGACAGGGTCAGCATCACCTGCAAGGCCAGTCAGGATGTGTATAATGC

TGTTGCCTGGTATCAACAGAAACCAGGACAATCTCCTAAACTTCTGATTT

ACTCGGCATCCTCCCGGTACACTGGAGTCCCTTCTCGCTTCACTGGCAGT

GGCTCTGGGCCGGATTTCACTTTCACCATCAGCAGTGTGCAGGCTGAAGA

CCTGGCAGTTTATTTCTGTCAGCAACATTTTCGTACTCCATTCACGTTCG

GCTCGGGGACAAAATTGGAGATCAAA.

An amino acid sequence of a CD28 transmembrane domain is shown in SEQ ID NO: 15:

KIEVMYPPPYLDNEKSNGTIIHVKGKHLCPSPLFPGPSKPFWVLVVVGGV

LACYSLLVTVAFIIFWVRSKRSRLLHSDYMNMTPRRPGPTRKHYQPYAPP

RDFAAYRS.

A nucleotide sequence of a CD28 transmembrane domain is shown in SEQ ID NO: 16:

AAAATTGAAGTTATGTATCCTCCTCCTTACCTAGACAATGAGAAGAGC

AATGGAACCATTATCCATGTGAAAGGGAAACACCTTTGTCCAAGTCCC

CTATTTCCCGGACCTTCTAAGCCCTTTTGGGTGCTGGTGGTGGTTGGT

GGAGTCCTGGCTTGCTATAGCTTGCTAGTAACAGTGGCCTTTATTATT

TTCTGGGTGAGGAGTAAGAGGAGCAGGCTCCTGCACAGTGACTACATG

AACATGACTCCCCGCCGCCCCGGGCCCACCCGCAAGCATTACCAGCCC

TATGCCCCACCACGCGACTTCGCAGCCTATCGCTCC.

An amino acid sequence of CD3ζ is shown in SEQ ID NO: 17:

APAYQQGQNQLYNELNLGRREEYDVLDKRRGRDPEMGGKPQRRKNPQE

GLYNELQKDKMAEAYSEIGMKGERRRGKGHDGLYQGLSTATKDTYDAL

HMQALPPR.

A nucleotide sequence of CD3ζ is shown in SEQ ID NO: 18:

GCCCCCGCGTACCAGCAGGGCCAGAACCAGCTCTATAACGAGCTCAAT

CTAGGACGAAGAGAGGAGTACGATGTTTTGGACAAGAGACGTGGCCGG

GACCCTGAGATGGGGGGAAAGCCGCAGAGAAGGAAGAACCCTCAGGAA

GGCCTGTACAATGAACTGCAGAAAGATAAGATGGCGGAGGCCTACAGT

GAGATTGGGATGAAAGGCGAGCGCCGGAGGGGCAAGGGGCACGATGGC

-continued
CTTTACCAGGGTCTCAGTACAGCCACCAAGGACACCTACGACGCCCTT

CACATGCAGGCCCTGCCCCCTCGCTAA.

An amino acid of Furin-P2A is shown in SEQ ID NO: 19:

RRKRSGSGEGRGSLLTCGDVEENPGP.

A coding nucleotide sequence of Furin-P2A is shown in SEQ ID NO: 20:

AGCGGCAGCGGCGAGGGAAGAGGAAGCCTGCTGACCTGCGGCGATG

TGGAGGAGAATCCCGGCCCCAGGAGGAAGAGA.

An amino acid sequence of a signal peptide of PD-L1 is shown in SEQ ID NO: 11, and a nucleotide sequence of the signal peptide of PD-L1 is shown in SEQ ID NO: 12.

An amino acid sequence of PD-L1scFv antibody is shown in SEQ ID NO: 21:

DIQMTQSPSSLSASVGDRVTITCRASQDVSTAVAWYQQKPGKAPKLLIYS

ASFLYSGVPSRFSGSGSGTDFTLTISSLQPEDFATYYCQQYLYHPATFGQ

GTKVEIKGGGGSGGGGSGGGGSEVQLVESGGGLVQPGGSLRLSCAASGFT

FSDSWIHWVRQAPGKGLEWVAWISPYGGSTYYADSVKGRFTISADTSKNT

AYLQMNSLRAEDTAVYYCARRHWPGGFDYWGQGTLVTVSA.

A coding nucleotide sequence of PD-L1scFv antibody is shown in SEQ ID NO: 22:

GACATCCAAATGACCCAGAGCCCTAGCTCCCTGTCCGCTAGCGTGGGC

GACAGGGTGACCATCACCTGCAGAGCCAGCCAGGACGTGAGCACCGCC

GTGGCCTGGTACCAGCAGAAGCCCGGCAAGGCCCCCAAGCTGCTGATC

TACAGCGCCTCCTTCCTGTACTCCGGCGTGCCCTCCAGATTTAGCGGC

AGCGGCAGCGGCACAGACTTCACCCTCACCATCAGCTCCCTGCAGCCT

GAGGACTTCGCCACATACTACTGCCAGCAGTACCTCTACCACCCTGCC

ACCTTCGGCCAAGGCACCAAGGTGGAGATCAAGGGCGGCGGAGGTTCT

GGCGGAGGCGGCTCCGGAGGAGGAGGCAGCGAAGTGCAGCTGGTGGAG

AGCGGAGGAGGACTGGTGCAGCCTGGCGGAAGCCTGAGGCTGAGCTGT

GCTGCCAGCGGCTTCACCTTCTCCGACTCCTGGATTCATTGGGTCAGG

CAGGCCCCCGGAAAAGGACTGGAGTGGGTCGCCTGGATCTCCCCTTAC

GGCGGCAGCACCTACTACGCCGACAGCGTGAAGGGCAGGTTCACCATC

AGCGCCGATACCAGCAAGAACACCGCCTACCTGCAGATGAACTCCCTG

AGGGCTGAGGACACCGCCGTGTACTACTGCGCCAGGAGGCACTGGCCT

GGCGGATTCGACTACTGGGGCCAGGGCACCCTGGTGACCGTGTCCGCC.

An amino acid sequence of the CD8 transmembrane domain is shown in SEQ ID NO: 23:

AAAFVPVFLPAKPTTTPAPRPPTPAPTIASQPLSLRPEACRPAAGGAV

HTRGLDFACDIYIWAPLAGTCGVLLLSLVITLYCNHRNRFSVV.

A nucleotide sequence of the CD8 transmembrane domain is shown in SEQ ID NO: 24:

GCGGCCGCATTCGTGCCGGTCTTCCTGCCAGCGAAGCCCACCACGAC

GCCAGCGCCGCGACCACCAACACCGGCGCCCACCATCGCGTCGCAGC

CCCTGTCCCTGCGCCCAGAGGCGTGCCGGCCAGCGGCGGGGGCGCA

GTGCACACGAGGGGGCTGGACTTCGCCTGTGATATCTACATCTGGGC

GCCCTTGGCCGGGACTTGTGGGGTCCTTCTCCTGTCACTGGTTATCA

CCCTTTACTGCAACCACAGGAACCGTTTCTCTGTTGTT.

An amino acid sequence of 4-1BB is shown in SEQ ID NO: 25:

KRGRKKLLYIFKQPFMRPVQTTQEEDGCSCRFPEEEEGGCEL.

A nucleotide sequence of 4-1BB is shown in SEQ ID NO: 26:

AAACGGGGCAGAAAGAAACTCCTGTATATATTCAAACAACCATTTATG

AGACCAGTACAAACTACTCAAGAGGAAGATGGCTGTAGCTGCCGATTT

CCAGAAGAAGAAGAAGGAGGATGTGAACTG.

Figure 2:
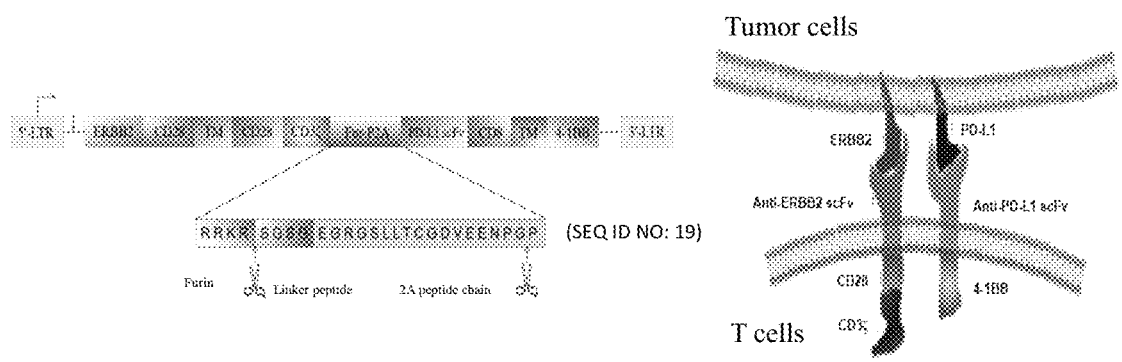
FIG. 2 is a schematic diagram of a preferred embodiment for a dual-targeting CAR binding HER2 and PD-L1.

A dual-targeting chimeric antigen receptor was synthesized according to the above sequences and inserted into a BamH1-NdeI site (see FIG. 2) of a lentiviral pWPXLd vector (Invitrogen), and then transformed into competent cells of *Escherichia coli*. After accurate sequencing, plasmids were extracted and purified with a plasmid purification kit from Qiagen by referring to the Kit Instructions for the purification steps to obtain high quality plasmids of the recombinant expression vector. Results of the inserted target fragments are shown in FIG. 1.

Example 2 Transformation of Cells with Recombinant Vector

1. Culture and Passage of 293T Cells:

A biosafety cabinet was opened, then the countertop was wiped with 75% alcohol cotton, and pipettes, pipette tip boxes, 15 ml centrifuge tubes, a centrifuge tube rack and 10 cm² new cell culture dishes were put in the biosafety cabinet. After the cabinet door was closed, a UV switch of the biosafety cabinet was turned on to irradiate for half an hour for disinfection and sterilization. DMEM containing 10% fetal bovine serum and 100 U/ml penicillin streptomycin and pancreatin were preheated in a 37° C. water bath. The biosafety cabinet was opened, a ventilation switch was turned on, and the culture dish for 293T cells grown to 80%-90% was taken out of a 37° C. incubator with 5% $CO_2$ and put into the biosafety cabinet. The hands, mouth of a medium bottle and a pipette cylinder were disinfected with 75% alcohol. Medium in the culture dish was pipetted completely with a sterile pipette and discarded into a disposal bottle, then 1 ml of pancreatin was added to roughly rinse off residual medium in the dish to neutralize a pancreatin inhibitor, and the resulting mixture was subsequently pipetted completely and removed. Next, 1-2 ml of pancreatin was added to the culture dish dropwise, cells were observed microscopically, and the pancreatin was pipetted after the cells became round and separated. Then 6-8 ml of fresh complete medium was added to the culture dish, and the cells were gently blown down. The cell suspension was divided and put into other culture dishes, and a medium was added to a volume of 10 ml per dish. The culture dishes were shaken several times in a cross way for mixing the cells well and put into a 37° C. incubator after observation under a microscope. The cell state was observed 24 h later, and the next subculture was carried out when the cells grew to 80%-90%.

2. Acquisition of Lentiviral Stock Solution:

Day 1: plating. 90% density of 293T cells were digested, subcultured at 1:5, and cultured overnight at 37° C. with 5% $CO_2$ in an approximately $1.0 \times 10^7$ cells/20 ml/15 cm dish. The cell density at 24 h was about 50-70% (no more than 70%). Day 2: transfection. The culture solution was changed 2 h before transfection, i.e., 20 ml preheated 10% DMEM medium with high glucose/dish. All reagents were balanced to room temperature. Transfection steps: a. A DNA mixture of 22.5 μg psPAX2 (packaging plasmid), 11.25 μg pMD.2G (envelope plasmid) and 22.5 μg pWPXLd (lentiviral vector) was prepared in a 50 ml BD tube (per 15 cm² dish); b. Water was added to 1125 μl; c. 125 μl of 2.5M $CaCl_2$ was added to the DNA solution dropwise and vortexed for 5 s; d. The BD tube was placed on a vortexer (gear 4), then a 2×BBS (1250 μl) solution was added to the DNA-$CaCl_2$ mixture dropwise before oscillation for 5 s; e. The resulting solution was allowed to stand at room temperature for 15 min, then 2.25 ml of transfection mixture was added to the dishes dropwise, gently shaken and mixed well in a cross way (10 times each), and cultured at 37° C. with 3% $CO_2$ (12-16 h). The medium was pipetted and washed once with 10 ml PBS. The culture solution was changed, i.e., 15 ml of preheated 5% DMEM medium, and cultured at 37° C. with 5% $CO_2$ to 48 h. Day 4: 48 h after transfection, the cell supernatant was collected, then 15 ml of preheated 5% FBS fresh DMEM medium was added, and cultured at 37° C. with 5% $CO_2$; the viral supernatant was filtered through a 0.45 μm filter and stored at 4° C. (no more than 1 week). Day 5: 72 h after transfection, the viral supernatant was collected, filtered through a 0.45 μm filter and stored at 4° C.

3. Concentration of Lentivirus:

Instruments: ultra-speed centrifuge, matched rotor and sleeves, ultra-speed centrifuge tubes and balancing balance. The sleeves and a balance were disinfected under a UV meter in the biosafety cabinet. Appropriate centrifuge tubes were placed into the sleeves after ensuring that there is no droplet in each sleeve. A viral suspension filtered through a 0.45 um filter was added to the centrifuge tubes. All centrifuge tubes filled with the viral suspension were strictly balanced by using a balance with accuracy of 0.001 g or above. With the sleeves covered, the balance was used again to verify whether the centrifuge tubes were completely balanced. The balanced sleeves were loaded into the rotor of the centrifuge, and prepared for centrifugation. Centrifugation: centrifugation conditions: 20° C., 70000×g, 2 h; wait until the speed of the centrifuge rises to 70000×g before the centrifugation. After centrifugation, the medium was poured off, and the centrifuge tubes were placed upside down on sterilized filter paper to absorb the remaining medium. The viral precipitate was resuspended with commercially available PBS, with the amount of PBS in each centrifuge tube depending on respective needs, generally 100 μl for each centrifuge tube. Finally, each centrifuge tube was washed with 100 μl of PBS and the eluate was pipetted. The resuspended virus was filled into small EP tubes and stored in a −80° C. refrigerator for later use.

Figure 3:
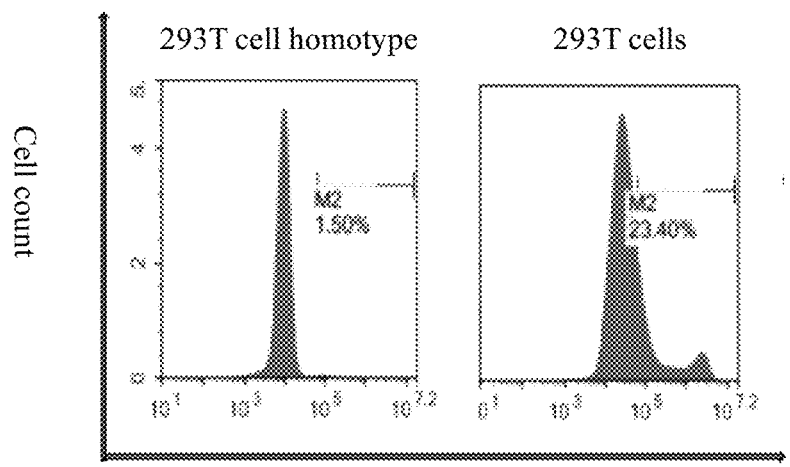
FIG. 3 is a flow chart for measuring CAR molecule expression on surfaces of 293T cells.

4. Detection of CAR Molecule Expression on Surfaces of 293T Cells Infected with Concentrated Viral Solution 293Td cells were infected with the HER2-PDL1 dual-CAR viral supernatant. 293Td cells were spread on a 6-well plate, and viral supernatant at 48 h was collected. The cells were infected with the supernatant and 10% FBS medium mixture (the supernatant: 10% FBS medium=1:1, 1 ml each), 2 ml of 10% FBS medium was changed at 24 h, and flow cytometry was carried out at 48 h to detect CAR expression (see FIG. 3).

5. Separation of Human Peripheral Blood T Lymphocytes:

Blood was taken into anticoagulation tubes, generally 15-20 ml at a time. A FICOLL lymphocyte separation medium was slowly added dropwise to the extracted blood at a ratio of lymphocyte separation medium to blood of 1:1. The mixture of lymphocyte separation medium and blood was centrifuged at 1000×g and 32° C. for 45 min, the rotate speed was increased/decreased at 3. After centrifugation, it could be seen that the blood was divided into 3 layers, and the layer where lymphocytes were present was an intermediate transparent layer. Lymphocytes in the intermediate transparent layer were pipetted slowly through a pipette tip, without pipetting liquid in the other two layers. The pipetted lymphocytes were added to a 20 mL serum-free and antibiotic-free X-VIVO medium and centrifuged at 500×g for 10 min. With the supernatant removed, the precipitated lymphocytes were resuspended with a 10 mL sterile red blood cell lysis buffer, with the lysis time not exceeding 5 min (2-3 min was sufficient). Then the precipitated lymphocytes were centrifuged at 500×g for 10 min. The supernatant was removed, then T lymphocytes were resuspended in 4 ml of 5% human AB serum, 2.5% IL-2 X-vivo medium and ready-for-use X-VIVO medium containing serum and IL-2, followed by cell counting, and the amount of medium added to each well of the 6-well plate was determined according to the cell count, generally with a volume of $3 \times 10^6$ lymphocytes per well. However, the exact amount to be added was calculated based on the titer of the virus and the amount used to kill experimental cells.

On the day before viral infection of T cells, the 6-well plate to be used in the viral infection experiment was coated with a RetroNectin diluent (RetroNectin was diluted with PBS to a concentration of 50 μg/ml), and each well of the six-well plate was coated with 2 ml of diluted RetroNectin. Then the six-well plate was sealed at 4° C. overnight for later use. On the day of infection, the RetroNectin diluent was pipetted, and the 6-well plate was sealed with a 2% BSA (bovine serum albumin) solution (prepared with PBS) for 30 min. After BSA was pipetted, the 6-well plate was rinsed several times with PBS (after the step, the 6-well plate can be stored at 4° C. for one week). For each well, 1 ml lentiviral suspension was prepared, mixed well and added to the 6-well plate for centrifugation at 32° C. and 1000×g for 2 h. The 6-well plate was taken out, and rinsed once with PBS after the supernatant was pipetted off. Each well was added with 2 mL of PBMC cell suspension at a concentration of $1.5 \times 10^6$ cell/mL. Then centrifuged at 32° C. and 1000×g for 10 min. Then the 6-well plate was cultured in a 37° C. incubator with 5% $CO_2$, and the culture solution was changed 48 h later. During the lentiviral infection, an MOI value between 4 and 40 is optimal.

Figure 4:
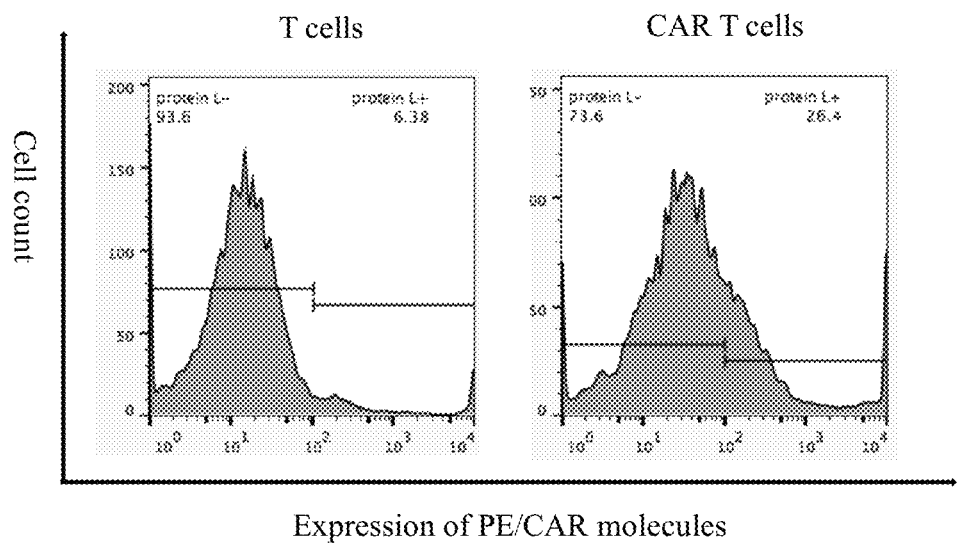
FIG. 4 is a flow chart for measuring CAR molecule expression on surfaces of T cells.

6. Detection of CAR Molecule Expression on Surfaces of T Cells after Infection of T Cells with Concentrated Virus:

T cells were infected with the HER2-PDL1 dual-CAR viral supernatant. 293Td cells were spread on a 6-well plate, and viral supernatant at 48 h was collected. The cells were infected with the supernatant and 10% medium mixture (the supernatant: 10% medium=1:1, 1 ml each), 2 mL of 10% medium was changed at 24 h, and flow cytometry was carried out at 48 h to detect CAR expression (see FIG. 4).

Screening of target cells: HER2 and/or PDL1-positive tumor cell lines (see FIG. 5) were screened by flow antibody molecule staining, constructing stable target cells/cell strains.

Figure 5:
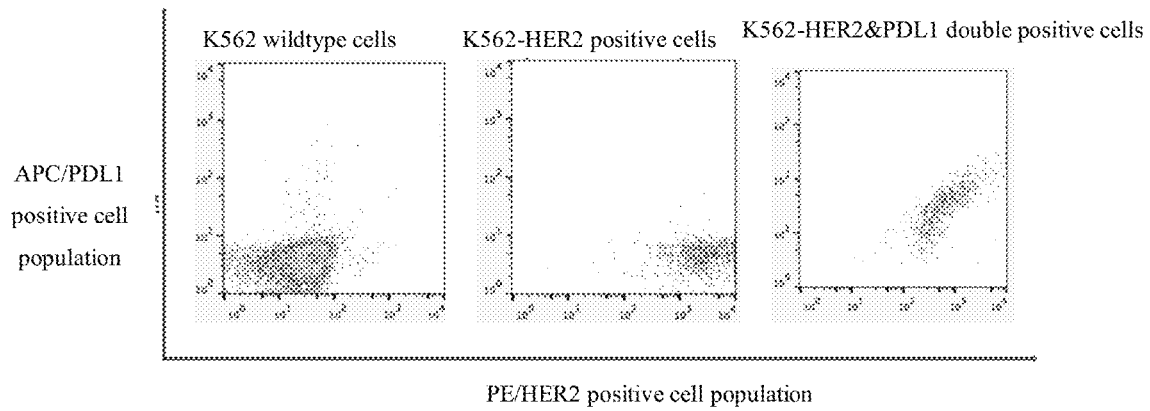
FIG. 5 is a flow chart for constructing a stable cell strain.

K562 cell lines are HER2 and PDL1 double negative cell lines, and K562 cell lines capable of stably expressing HER2 and/or PDL1 molecules were constructed by means of lentiviral infection to transfer HER2 and/or PDL1 molecules (see FIG. 5).

Culturing of CAR-Ts:

Peripheral blood mononuclear cells separated from a lymphocyte separation medium (Fillco) by density gradient centrifugation were counted with a cell counting plate to acquire total cell count, and then the same number of identical CD3/CD28 magnetic beads (Gibco) were added at a ratio of 1:1. In the presence of a magnetic rack, about 10 mL of X-VIVO medium was added to a 50 mL BD tube, and then the actual volume of magnetic beads calculated by counting was added. After gently blowing for resuspension, the BD tube was placed in the magnetic rack and allowed to stand for 3-4 min, leaving only pure magnetic beads adsorbed on the wall of the BD tube. Peripheral blood mononuclear cells (PBMCs) resuspended with X-VIVO were added to the BD tube. The concentration of the PBMCs was controlled as much as possible at $1-2\times10^6$/mL, followed by blowing with a pipette for resuspension. Commercial human AB serum (sigma) with a volume of 5% of the total medium volume was added. With the density of T cells controlled at $1-2\times10^6$/mL, up to $3\times10^6$ T cells could be cultured in one well of a 6-well plate, beyond which T cells could be distributed to 2 wells, and so on. The culture solution was changed at least once every 48 h, or once every 24 h and readjust the cell density if the medium showed obvious yellowing. In the culture of T cells, the clonal morphology was observed every 24 h to know the morphological changes of T cells, the tendency of apoptotic senescence and the presence of fungal bacterial contamination. Meanwhile, the total amount of T cells was estimated. Every time the culture solution was changed, serum and IL-2 were dissolved and prepared in real time. It is recommended that T cells are centrifuged at 1300 rpm/min at room temperature for 3 min with 5 mL BD tubes as centrifuge tubes.

Example 3 Determination of Performance of Dual-Target CAR-Ts of HER2 and PDL1

1. Determination of In Vitro Killing Ability of CAR-Ts

Figure 7:
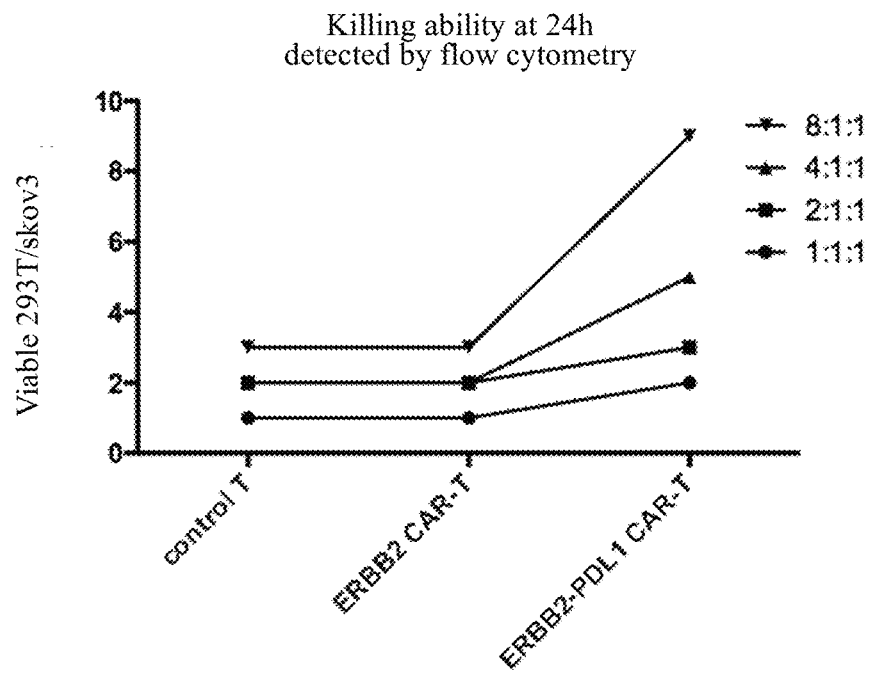
FIG. 7 shows the results of in vitro killing by genetically engineered T cells, and the ratio of viable negative cells and positive cells (T includes three cell types: T, HER2 CAR-T and HER2/PD-L1 CAR-T; k is short for k562, herk for k562-her2, and hlk for k562-her2-pdl1)

Effector cells and target cells were stained with a Cell Trace™ CFSE Cell Proliferation Kit (Thermo) and a Cell Trace™ Far Red Cell Proliferation Kit (Thermo) respectively. The effector cells (e.g., T cells and CAR-Ts) and the target cells (e.g., SKOV3 and 293T cells) were added to a 12-well plate at a ratio of effector cells:target cells (E:T) of 1:1, 2:1, 4:1 and 8:1, with $1*10^6$ target cells in each well, and control wells with only effector cells or target cells were added. Among them, SKOV3 was target cells and 293T cell was control negative cells. Results of flow cytometry were observed, and the death or proliferation of the target cells reflected the in vitro killing ability of CAR-Ts (see FIG. 7). The results in FIG. 7 show that the in vitro killing ability of dual-targeting CAR-Ts of HER2 and PDL1 to tumor cells is obviously better than that of single-targeting CAR-Ts of HER2 to the same tumor cells, and even better than that of simple T cells to the same tumor cells.

2. Evaluation the Killing Ability of CAR-Ts and IFN-γ Secretion In Vitro

Figure 6:
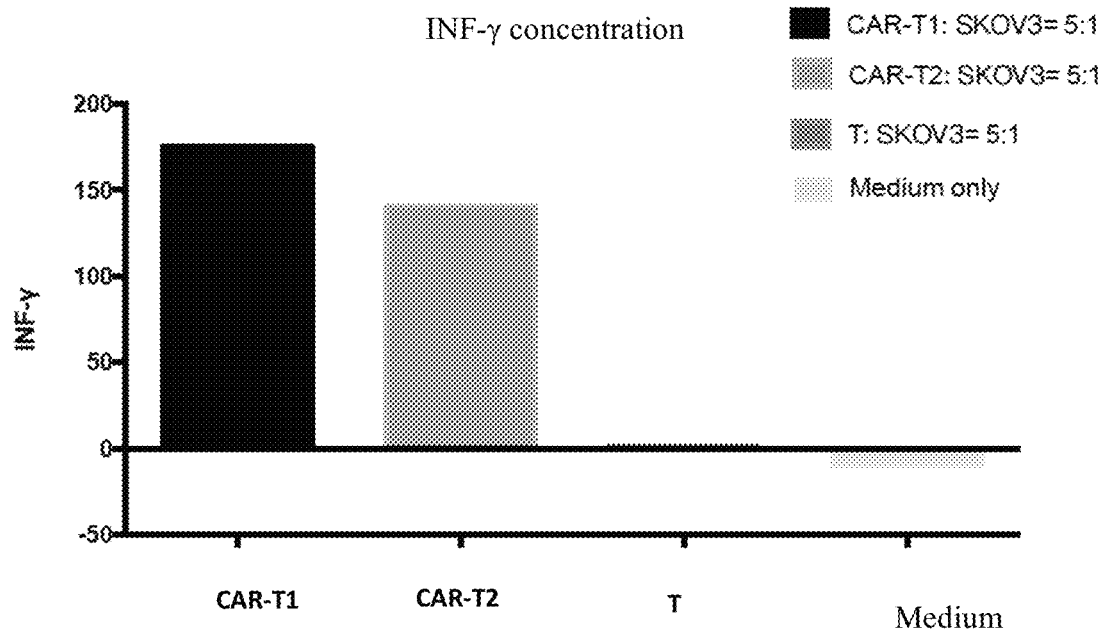
FIG. 6 shows the secretion of IFN-γ results of in vitro killing by two types of CAR-Ts and control T cells.

An IFN gamma Human ELISA Kit (Thermo) was used, the number of strips required for an experiment was calculated, required strips were taken out and put in a frame, while temporarily unused strips were put back into sealed aluminum foil bags and stored at 4° C. It was recommended to set a background correction well, i.e., a blank well, by simply adding a TMB substrate and a stop buffer to the well. A standard control was required and a standard curve was plotted for each experiment. Samples or standards at different concentrations (100 μl/well) were added to the corresponding wells, and reaction wells were sealed with sealing tape and incubated at room temperature for 120 min. For serum or plasma samples, 50 μl of sample analysis buffer and 50 μl of samples were added successively. For the large dilution volume, the samples and the sample analysis buffer were added in an equal amount. The plate was washed for 5 times and dried on thick absorbent paper at the last time. A biotinylated antibody working solution was added (100 μl/well), and reaction wells were sealed with sealing tape and incubated at room temperature for 60 min. The plate was washed for 5 times and dried on thick absorbent paper at the last time. An enzyme conjugate working solution was added (100 μl/well), and reaction wells were sealed with sealing tape and incubated at room temperature away from light for 20 min. The plate was washed for 5 times and dried on thick absorbent paper at the last time. A color developing agent TMB was added (100 μl/well), then the plate was incubated at room temperature away from light for 20 min, and a stop buffer was added (50 μl/well) to measure OD450 immediately after mixing. Judgment of results: the results are valid only when the values of replicate wells are within 20% of the difference range, and mean values of the replicate wells can be used as measured values; and the OD value of each standard or sample should be subtracted from the OD value of the background correction well to plot a standard curve. With the concentrations of standards as the X-coordinate and OD values as the Y-coordinate, coordinate points of the standards are connected by a smooth line. The concentration of each sample can be found on the standard curve by the corresponding OD value; if the OD value of the sample is higher than the upper limit of the standard curve, the sample should be re-tested after appropriate dilution, and the concentration should be calculated by multiplying the dilution factor (see FIG. 6). The results in FIG. 6 show that the in vitro killing ability of dual-target CAR-Ts of ERBB2 and PDL1 to tumor cells is obviously better than that of simple T cells to the same tumor cells.

Figure 8:
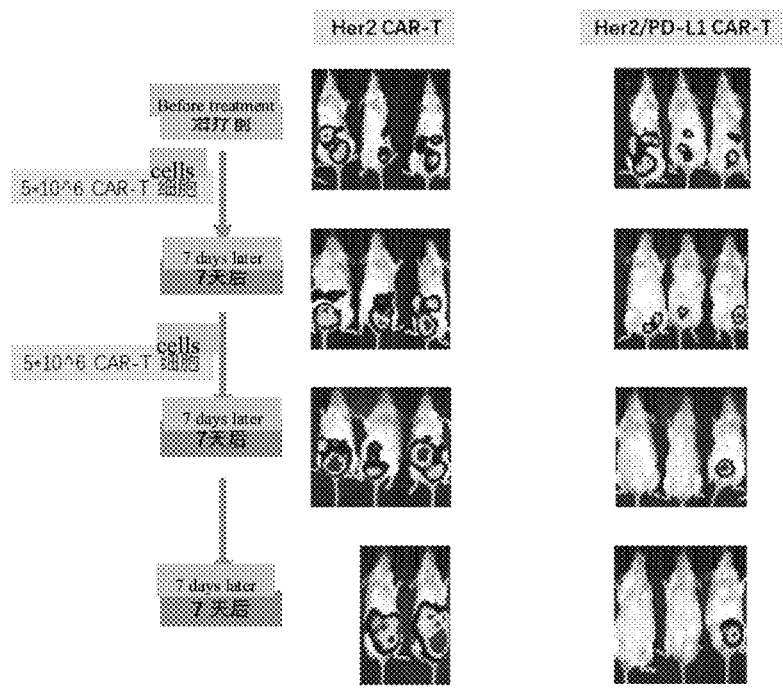
FIG. 8 shows the results of HER2 CAR-T and HER2/PD-L1 CAR-T in treating intraperitoneal implantation models of ovarian cancer SKOV3 in vivo.

3. HER2 CAR-Ts and HER2/PD-L1 Dual-Targeting CAR-Ts for Treatment of Intraperitoneal Implantation Models of Ovarian Cancer SKOV3 in Mice Intraperitoneal models of ovarian cancer SKOV3 in mice. Female 8-12 week old NOD.Cg-PrkdcscidIl2rgtmWjl/SzJ (NSG) mice were selected, and injected intraperitoneally with $5\times10^5$ FLuc-GFP SKOV3 cells. Different types of $5\times10^6$ CAR T cells were injected intraperitoneally 10 days later, and the second intraperitoneal injection of CAR-Ts was performed 7 days later. Tumor burden was measured by bioluminescence imaging with a Xenogen IVIS imaging system (Xenogen) every 7 days from the first injection of CAR-Ts. The acquired bioluminescence data were analyzed by Living Image software (Xenogen). According to the results in FIG. 8, dual-targeting CAR-Ts of HER2/PDL1 were significantly more efficacious than HER2 CAR-Ts in the treatment of intraperitoneal models of SKOV3 in mice.

According to the above test results, the dual-targeting chimeric antigen receptor containing HER2 and PD-L1 constructed in the present invention had a certain anti-tumor effect in vitro, and the in vitro tests have verified the efficiency thereof, providing a more effective treatment method for malignant tumors. The results showed that the in vitro killing ability of dual-targeting CAR-Ts of HER2 and PDL1 provided by the present invention to tumor cells is obviously better than that of single-targeting CAR-Ts of HER2 to the same tumor cells, and even better than that of simple T cells to the same tumor cells.

The invention claimed is:

1. A genetically engineered dual-targeting chimeric antigen receptor, comprising:
   (a) a chimeric antigen receptor 1 comprising:
      (1) an scFv antibody of human HER2, a CD28 transmembrane domain and a CD3ζ binding domain, which has the amino acid sequence shown in SEQ ID NO: 5 and/or is encoded by the nucleotide sequence shown in SEQ ID NO: 6; or
      (ii) an scFv antibody of human VEGFR1, a CD28 transmembrane domain and a CD3ζ binding domain, which has the amino acid sequence shown in SEQ ID NO: 3 and/or is encoded by the nucleotide sequence shown in SEQ ID NO: 4;
   (b) a chimeric antigen receptor 2 capable of recognizing PD-L1, which comprises a scFv antibody of human PD-L1, a CD8 transmembrane domain and a 4-1BB costimulatory molecular peptide fragment, and has the amino acid sequence shown in SEQ ID NO: 1 and/or is encoded by the nucleotide sequence shown in SEQ ID NO: 2; and
   (c) a linker peptide linking the chimeric antigen receptor 1 with the chimeric antigen receptor 2.

2. The dual-targeting chimeric antigen receptor according to claim 1, wherein the linker peptide is at least one of Furin and P2A.

3. The dual-targeting chimeric antigen receptor according to claim 1, wherein the chimeric antigen receptor 1 comprises the scFv antibody of human VEGFR1, the CD28 transmembrane domain and the CD3ζ binding domain, and has the amino acid sequence shown in SEQ ID NO: 3.

4. The dual-targeting chimeric antigen receptor according to claim 3, wherein the linker peptide is at least one of Furin and P2A.

5. The dual-targeting chimeric antigen receptor according to claim 1, wherein the chimeric antigen receptor 1 comprises the scFv antibody of human VEGFR1, the CD28 transmembrane domain and the CD3ζ binding domain, and is encoded by the nucleotide sequence shown in SEQ ID NO: 4.

6. The dual-targeting chimeric antigen receptor according to claim 5, wherein the linker peptide is at least one of Furin and P2A.

7. The dual-targeting chimeric antigen receptor according to claim 1, wherein the chimeric antigen receptor 1 comprises the scFv antibody of human HER2, the CD28 transmembrane domain and the CD3ζ binding domain, and has the amino acid sequence shown in SEQ ID NO: 5.

8. The dual-targeting chimeric antigen receptor according to claim 7, wherein the linker peptide is at least one of Furin and P2A.

9. The dual-targeting chimeric antigen receptor according to claim 1, wherein the chimeric antigen receptor 1 comprises the scFv antibody of human HER2, the CD28 transmembrane domain and the CD3ζ binding domain, and is encoded by the nucleotide sequence shown in SEQ ID NO: 6.

10. The dual-targeting chimeric antigen receptor according to claim 9, wherein the linker peptide is at least one of Furin and P2A.

11. The dual-targeting chimeric antigen receptor according to claim 1, wherein the chimeric antigen receptor 1 and the chimeric antigen receptor 2 are co-expressed by a vector.

12. An expression vector for simultaneous expression of the dual-targeting chimeric antigen receptor according to claim 1.

13. A host cell containing the expression vector according to claim 12.

* * * * *

SEQUENCE LISTING

```
<160> NUMBER OF SEQ ID NOS: 26

<210> SEQ ID NO 1
<211> LENGTH: 373
<212> TYPE: PRT
<213> ORGANISM: Artificial Sequence
<220> FEATURE:
<223> OTHER INFORMATION: synthetic

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Ser Glu Val Gln Leu Val Glu
        115                 120                 125

Ser Gly Gly Gly Leu Val Gln Pro Gly Gly Ser Leu Arg Leu Ser Cys
130                 135                 140

Ala Ala Ser Gly Phe Thr Phe Ser Asp Ser Trp Ile His Trp Val Arg
145                 150                 155                 160

Gln Ala Pro Gly Lys Gly Leu Glu Trp Val Ala Trp Ile Ser Pro Tyr
                165                 170                 175

Gly Gly Ser Thr Tyr Tyr Ala Asp Ser Val Lys Gly Arg Phe Thr Ile
            180                 185                 190

Ser Ala Asp Thr Ser Lys Asn Thr Ala Tyr Leu Gln Met Asn Ser Leu
        195                 200                 205

Arg Ala Glu Asp Thr Ala Val Tyr Tyr Cys Ala Arg Arg His Trp Pro
    210                 215                 220

Gly Gly Phe Asp Tyr Trp Gly Gln Gly Thr Leu Val Thr Val Ser Ala
225                 230                 235                 240

Ala Ala Ala Phe Val Pro Val Phe Leu Pro Ala Lys Pro Thr Thr Thr
                245                 250                 255

Pro Ala Pro Arg Pro Pro Thr Pro Ala Pro Thr Ile Ala Ser Gln Pro
            260                 265                 270

Leu Ser Leu Arg Pro Glu Ala Cys Arg Pro Ala Ala Gly Gly Ala Val
        275                 280                 285

His Thr Arg Gly Leu Asp Phe Ala Cys Asp Ile Tyr Ile Trp Ala Pro
    290                 295                 300

Leu Ala Gly Thr Cys Gly Val Leu Leu Leu Ser Leu Val Ile Thr Leu
305                 310                 315                 320
```

Tyr Cys Asn His Arg Asn Arg Phe Ser Val Val Lys Arg Gly Arg Lys
            325                 330                 335

Lys Leu Leu Tyr Ile Phe Lys Gln Pro Phe Met Arg Pro Val Gln Thr
            340                 345                 350

Thr Gln Glu Glu Asp Gly Cys Ser Cys Arg Phe Pro Glu Glu Glu Glu
            355                 360                 365

Gly Gly Cys Glu Leu
        370

<210> SEQ ID NO 2
<211> LENGTH: 1122
<212> TYPE: DNA
<213> ORGANISM: Artificial Sequence
<220> FEATURE:
<223> OTHER INFORMATION: synthetic

<400> SEQUENCE: 2

```
gacatccaaa tgacccagag ccctagctcc ctgtccgcta gcgtgggcga cagggtgacc      60
atcacctgca gagccagcca ggacgtgagc accgccgtgg cctggtacca gcagaagccc     120
ggcaaggccc ccaagctgct gatctacagc gcctccttcc tgtactccgg cgtgccctcc     180
agatttagcg gcagcggcag cggcacagac ttcaccctca ccatcagctc cctgcagcct     240
gaggacttcg ccacatacta ctgccagcag tacctctacc accctgccac cttcggccaa     300
ggcaccaagg tggagatcaa gggcggcgga ggttctggcg gaggcggctc cggaggagga     360
ggcagcgaag tgcagctggt ggagagcgga ggaggactgg tgcagcctgg cggaagcctg     420
aggctgagct gtgctgccag cggcttcacc ttctccgact cctggattca ttgggtcagg     480
caggcccccg gaaaaggact ggagtgggtc gcctggatct cccctacgg cggcagcacc     540
tactacgccg acagcgtgaa gggcaggttc accatcagcg ccgataccag caagaacacc     600
gcctacctgc agatgaactc cctgagggct gaggacaccg ccgtgtacta ctgcgccagg     660
aggcactggc ctggcggatt cgactactgg ggccagggca cctggtgac cgtgtccgcc     720
gccgccgcct tcgtgcctgt gtttctgccc gccaagccca ccaccacacc tgctcccaga     780
cctcccacac ctgcccctac catcgctagc agcccctga gctgagacc cgaggcttgt     840
aggcctgctg ctggcggagc cgtgcacaca gaggcctgg acttcgcctg cgacatctac     900
atctgggccc cctggccgg aacatgtgga gtgctgctgc tgagcctggt gatcaccctg     960
tactgcaacc acaggaacag gttcagcgtg gtgaagaggg gcaggaagaa gctgctgtac    1020
atcttcaagc agcccttcat gaggcccgtg cagaccaccc aggaggagga tggctgcagc    1080
tgcaggttcc ctgaagagga ggagggcggc tgcgagctgt ga                        1122
```

<210> SEQ ID NO 3
<211> LENGTH: 482
<212> TYPE: PRT
<213> ORGANISM: Artificial Sequence
<220> FEATURE:
<223> OTHER INFORMATION: synthetic

<400> SEQUENCE: 3

Met Ala Leu Pro Val Thr Ala Leu Leu Leu Pro Leu Ala Leu Leu Leu
1                 5                   10                  15

His Ala Ala Arg Pro Glu Ile Val Leu Thr Gln Ser Pro Gly Thr Leu
            20                  25                  30

Ser Leu Ser Pro Gly Glu Arg Ala Thr Leu Ser Cys Arg Ala Ser Gln
        35                  40                  45

```
Ser Val Ser Ser Ser Tyr Leu Ala Trp Tyr Gln Gln Lys Pro Gly Gln
    50                  55                  60
Ala Pro Arg Leu Leu Ile Tyr Gly Ala Ser Ser Arg Ala Thr Gly Ile
65                  70                  75                  80
Pro Asp Arg Phe Ser Gly Ser Gly Ser Gly Thr Asp Phe Thr Leu Thr
                85                  90                  95
Ile Ser Arg Leu Glu Pro Glu Asp Phe Ala Val Tyr Tyr Cys Gln Gln
            100                 105                 110
Tyr Gly Ser Ser Pro Leu Thr Phe Gly Gly Gly Thr Lys Val Glu Ile
        115                 120                 125
Lys Gly Gly Gly Gly Ser Gly Gly Gly Gly Ser Gly Gly Gly Gly Ser
130                 135                 140
Gln Ala Gln Val Val Glu Ser Gly Gly Gly Val Val Gln Ser Gly Arg
145                 150                 155                 160
Ser Leu Arg Leu Ser Cys Ala Ala Ser Gly Phe Ala Phe Ser Ser Tyr
            165                 170                 175
Gly Met His Trp Val Arg Gln Ala Pro Gly Lys Gly Leu Glu Trp Val
        180                 185                 190
Ala Val Ile Trp Tyr Asp Gly Ser Asn Lys Tyr Tyr Ala Asp Ser Val
    195                 200                 205
Arg Gly Arg Phe Thr Ile Ser Arg Asp Asn Ser Glu Asn Thr Leu Tyr
210                 215                 220
Leu Gln Met Asn Ser Leu Arg Ala Glu Asp Thr Ala Val Tyr Tyr Cys
225                 230                 235                 240
Ala Arg Asp His Tyr Gly Ser Gly Val His His Tyr Phe Tyr Tyr Gly
            245                 250                 255
Leu Asp Val Trp Gly Gln Gly Thr Thr Val Thr Val Ser Ser Lys Ile
        260                 265                 270
Glu Val Met Tyr Pro Pro Pro Tyr Leu Asp Asn Glu Lys Ser Asn Gly
    275                 280                 285
Thr Ile Ile His Val Lys Gly Lys His Leu Cys Pro Ser Pro Leu Phe
290                 295                 300
Pro Gly Pro Ser Lys Pro Phe Trp Val Leu Val Val Val Gly Gly Val
305                 310                 315                 320
Leu Ala Cys Tyr Ser Leu Leu Val Thr Val Ala Phe Ile Ile Phe Trp
            325                 330                 335
Val Arg Ser Lys Arg Ser Arg Leu Leu His Ser Asp Tyr Met Asn Met
        340                 345                 350
Thr Pro Arg Arg Pro Gly Pro Thr Arg Lys His Tyr Gln Pro Tyr Ala
    355                 360                 365
Pro Pro Arg Asp Phe Ala Ala Tyr Arg Ser Ala Pro Ala Tyr Gln Gln
370                 375                 380
Gly Gln Asn Gln Leu Tyr Asn Glu Leu Asn Leu Gly Arg Arg Glu Glu
385                 390                 395                 400
Tyr Asp Val Leu Asp Lys Arg Arg Gly Arg Asp Pro Glu Met Gly Gly
            405                 410                 415
Lys Pro Gln Arg Arg Lys Asn Pro Gln Glu Gly Leu Tyr Asn Glu Leu
        420                 425                 430
Gln Lys Asp Lys Met Ala Glu Ala Tyr Ser Glu Ile Gly Met Lys Gly
    435                 440                 445
Glu Arg Arg Arg Gly Lys Gly His Asp Gly Leu Tyr Gln Gly Leu Ser
450                 455                 460
```

```
Thr Ala Thr Lys Asp Thr Tyr Asp Ala Leu His Met Gln Ala Leu Pro
465                 470                 475                 480

Pro Arg
```

<210> SEQ ID NO 4
<211> LENGTH: 1446
<212> TYPE: DNA
<213> ORGANISM: Artificial Sequence
<220> FEATURE:
<223> OTHER INFORMATION: synthetic

<400> SEQUENCE: 4

```
atggccttac cagtgaccgc cttgctcctg ccgctggcct tgctgctcca cgccgccagg      60
ccggagatcg tgctgacaca gagccctggc accctgagcc tgtccccggg cgaaagagcc     120
accctgtcct gcagagccag ccagagcgtg agcagctcct atctggcctg gtaccagcag     180
aagcctggcc aggcccccag actcctgatc tacggcgcca gcagcagagc caccggcatc     240
cccgatagat tcagcggctc cggcagcgga accgacttta ccctgaccat ctccagactg     300
gagcccgagg actttgccgt gtactactgc cagcagtacg gcagcagccc cctgacattc     360
ggcggcggca caaggtgga gatcaaaggc ggcgaggtt ctggaggagg aggaagcgga     420
ggaggaggca gccaggctca ggtggtcgaa agcggcggag agtggtgca gagcggaagg     480
tccctgaggc tgagctgcgc tgctagcggc tttgccttct cctcctacgg catgcactgg     540
gtgagacagg cccctggcaa gggcctggaa tgggtggctg tgatctggta cgacggcagc     600
aacaagtact acgccgacag cgtgaggggc aggttcacca tcagcaggga caacagcgaa     660
aacaccctgt acctgcagat gaacagcctc agggccgagg ataccgccgt gtattattgc     720
gccagggatc actacggaag cggcgtgcac cattacttct attacggcct ggacgtgtgg     780
ggccagggca acagtgac cgtgtccagc aaaattgaag ttatgtatcc tcctccttac     840
ctagacaatg agaagagcaa tggaaccatt atccatgtga aagggaaaca cctttgtcca     900
agtcccctat ttcccggacc ttctaagccc ttttgggtgc tggtggtggt tggtggagtc     960
ctggcttgct atagcttgct agtaacagtg gcctttatta ttttctgggt gaggagtaag    1020
aggagcaggc tcctgcacag tgactacatg aacatgactc cccgccgccc cgggcccacc    1080
cgcaagcatt accagcccta tgccccacca cgcgacttcg cagcctatcg ctccgccccc    1140
gcgtaccagc agggccagaa ccagctctat aacgagctca atctaggacg aagagaggag    1200
tacgatgttt tggacaagag acgtggccgg gaccctgaga tggggggaaa gccgcagaga    1260
aggaagaacc ctcaggaagg cctgtacaat gaactgcaga agataagat ggcggaggcc    1320
tacagtgaga ttgggatgaa aggcgagcgc cggaggggca aggggcacga tggcctttac    1380
cagggtctca gtacagccac caaggacacc tacgacgccc ttcacatgca ggccctgccc    1440
cctcgc                                                               1446
```

<210> SEQ ID NO 5
<211> LENGTH: 475
<212> TYPE: PRT
<213> ORGANISM: Artificial Sequence
<220> FEATURE:
<223> OTHER INFORMATION: synthetic

<400> SEQUENCE: 5

```
Met Ala Leu Pro Val Thr Ala Leu Leu Leu Pro Leu Ala Leu Leu Leu
1               5                   10                  15

His Ala Ala Arg Pro Met Gln Val Gln Leu Gln Gln Ser Gly Pro Glu
```

```
                    20                  25                  30
Leu Lys Lys Pro Gly Glu Thr Val Lys Ile Ser Cys Lys Ala Ser Gly
                35                  40                  45
Tyr Pro Phe Thr Asn Tyr Gly Met Asn Trp Val Lys Gln Ala Pro Gly
50                  55                  60
Gln Gly Leu Lys Trp Met Gly Trp Ile Asn Thr Ser Thr Gly Glu Ser
65                  70                  75                  80
Thr Phe Ala Asp Asp Phe Lys Gly Arg Phe Asp Phe Ser Leu Glu Thr
                        85                  90                  95
Ser Ala Asn Thr Ala Tyr Leu Gln Ile Asn Asn Leu Lys Ser Glu Asp
                100                 105                 110
Ser Ala Thr Tyr Phe Cys Ala Arg Trp Glu Val Tyr His Gly Tyr Val
                115                 120                 125
Pro Tyr Trp Gly Gln Gly Thr Thr Val Thr Val Ser Ser Gly Gly Gly
                130                 135                 140
Gly Ser Gly Gly Gly Ser Gly Gly Gly Ser Asp Ile Gln Leu
145                 150                 155                 160
Thr Gln Ser His Lys Phe Leu Ser Thr Ser Val Gly Asp Arg Val Ser
                165                 170                 175
Ile Thr Cys Lys Ala Ser Gln Asp Val Tyr Asn Ala Val Ala Trp Tyr
                180                 185                 190
Gln Gln Lys Pro Gly Gln Ser Pro Lys Leu Leu Ile Tyr Ser Ala Ser
                195                 200                 205
Ser Arg Tyr Thr Gly Val Pro Ser Arg Phe Thr Gly Ser Gly Ser Gly
                210                 215                 220
Pro Asp Phe Thr Phe Thr Ile Ser Ser Val Gln Ala Glu Asp Leu Ala
225                 230                 235                 240
Val Tyr Phe Cys Gln Gln His Phe Arg Thr Pro Phe Thr Phe Gly Ser
                245                 250                 255
Gly Thr Lys Leu Glu Ile Lys Lys Ile Glu Val Met Tyr Pro Pro Pro
                260                 265                 270
Tyr Leu Asp Asn Glu Lys Ser Asn Gly Thr Ile Ile His Val Lys Gly
                275                 280                 285
Lys His Leu Cys Pro Ser Pro Leu Phe Pro Gly Pro Ser Lys Pro Phe
                290                 295                 300
Trp Val Leu Val Val Val Gly Gly Val Leu Ala Cys Tyr Ser Leu Leu
305                 310                 315                 320
Val Thr Val Ala Phe Ile Ile Phe Trp Val Arg Ser Lys Arg Ser Arg
                        325                 330                 335
Leu Leu His Ser Asp Tyr Met Asn Met Thr Pro Arg Arg Pro Gly Pro
                340                 345                 350
Thr Arg Lys His Tyr Gln Pro Tyr Ala Pro Pro Arg Asp Phe Ala Ala
                355                 360                 365
Tyr Arg Ser Ala Pro Ala Tyr Gln Gln Gly Gln Asn Gln Leu Tyr Asn
                370                 375                 380
Glu Leu Asn Leu Gly Arg Arg Glu Glu Tyr Asp Val Leu Asp Lys Arg
385                 390                 395                 400
Arg Gly Arg Asp Pro Glu Met Gly Gly Lys Pro Gln Arg Arg Lys Asn
                        405                 410                 415
Pro Gln Glu Gly Leu Tyr Asn Glu Leu Gln Lys Asp Lys Met Ala Glu
                420                 425                 430
Ala Tyr Ser Glu Ile Gly Met Lys Gly Glu Arg Arg Arg Gly Lys Gly
                435                 440                 445
```

His Asp Gly Leu Tyr Gln Gly Leu Ser Thr Ala Thr Lys Asp Thr Tyr
    450                 455                 460

Asp Ala Leu His Met Gln Ala Leu Pro Pro Arg
465                 470                 475

<210> SEQ ID NO 6
<211> LENGTH: 1428
<212> TYPE: DNA
<213> ORGANISM: Artificial Sequence
<220> FEATURE:
<223> OTHER INFORMATION: synthetic

<400> SEQUENCE: 6

```
atggccttac cagtgaccgc cttgctcctg ccgctggcct tgctgctcca cgccgccagg      60
ccgatgcagg tacaactgca gcagtcagga cctgaactga agaagcctgg agagacagtc     120
aagatctcct gcaaggcctc tgggtatcct ttcacaaact atggaatgaa ctgggtgaag     180
caggctccag acaggggttt aaagtggatg ggctggatta cacctccac tggagagtca     240
acatttgctg atgacttcaa gggacggttt gacttctctt tggaaacctc tgccaacact     300
gcctatttgc agatcaacaa cctcaaaagt gaagactcgg ctacatattt ctgtgcaaga     360
tgggaggttt accacggcta cgttccttac tggggccaag ggaccacggt caccgtttcc     420
tctggcggtg gcggttctgg tggcggtggc tccggcggtg gcggttctga catccagctg     480
acccagtctc acaaattcct gtccacttca gtaggagaca gggtcagcat cacctgcaag     540
gccagtcagg atgtgtataa tgctgttgcc tggtatcaac agaaaccagg acaatctcct     600
aaacttctga tttactcggc atcctcccgg tacactggag tcccttctcg cttcactggc     660
agtggctctg ggccggattt cactttcacc atcagcagtg tgcaggctga agacctggca     720
gtttatttct gtcagcaaca ttttcgtact ccattcacgt tcggctcggg gacaaaattg     780
gagatcaaaa aaattgaagt tatgtatcct cctccttacc tagacaatga aagagcaat     840
ggaaccatta tccatgtgaa agggaaacac ctttgtccaa gtcccctatt tcccggacct     900
tctaagccct ttgggtgct ggtggtggtt ggtggagtcc tggcttgcta tagcttgcta     960
gtaacagtgg cctttattat tttctgggtg aggagtaaga ggagcaggct cctgcacagt    1020
gactacatga acatgactcc ccgccgcccc gggcccaccc gcaagcatta ccagccctat    1080
gccccaccac gcgacttcgc agcctatcgc tccgccccg cgtaccagca gggccagaac    1140
cagctctata cgagctcaa tctaggacga agagaggagt acgatgtttt ggacaagaga    1200
cgtggccggg accctgagat ggggggaaag ccgcagagaa ggaagaaccc tcaggaaggc    1260
ctgtacaatg aactgcagaa agataagatg gcggaggcct acagtgagat tgggatgaaa    1320
ggcgagcgcc ggagggggcaa ggggcacgat ggcctttacc agggtctcag tacagccacc    1380
aaggacacct acgacgccct tcacatgcag gccctgcccc ctcgctaa                1428
```

<210> SEQ ID NO 7
<211> LENGTH: 22
<212> TYPE: PRT
<213> ORGANISM: Artificial Sequence
<220> FEATURE:
<223> OTHER INFORMATION: synthetic

<400> SEQUENCE: 7

Ser Gly Ser Gly Glu Gly Arg Gly Ser Leu Leu Thr Cys Gly Asp Val
1               5                   10                  15

Glu Glu Asn Pro Gly Pro

```
<210> SEQ ID NO 8
<211> LENGTH: 66
<212> TYPE: DNA
<213> ORGANISM: Artificial Sequence
<220> FEATURE:
<223> OTHER INFORMATION: synthetic

<400> SEQUENCE: 8
agcggcagcg gcgagggaag aggaagcctg ctgacctgcg gcgatgtgga ggagaatccc    60
ggcccc                                                               66

<210> SEQ ID NO 9
<211> LENGTH: 4
<212> TYPE: PRT
<213> ORGANISM: Artificial Sequence
<220> FEATURE:
<223> OTHER INFORMATION: synthetic

<400> SEQUENCE: 9

Arg Arg Lys Arg
1

<210> SEQ ID NO 10
<211> LENGTH: 12
<212> TYPE: DNA
<213> ORGANISM: Artificial Sequence
<220> FEATURE:
<223> OTHER INFORMATION: synthetic

<400> SEQUENCE: 10
aggaggaaga ga                                                         12

<210> SEQ ID NO 11
<211> LENGTH: 21
<212> TYPE: PRT
<213> ORGANISM: Artificial Sequence
<220> FEATURE:
<223> OTHER INFORMATION: synthetic

<400> SEQUENCE: 11

Met Ala Leu Pro Val Thr Ala Leu Leu Leu Pro Leu Ala Leu Leu Leu
1               5                   10                  15

His Ala Ala Arg Pro
            20

<210> SEQ ID NO 12
<211> LENGTH: 63
<212> TYPE: DNA
<213> ORGANISM: Artificial Sequence
<220> FEATURE:
<223> OTHER INFORMATION: synthetic

<400> SEQUENCE: 12
atggccttac cagtgaccgc cttgctcctg ccgctggcct tgctgctcca cgccgccagg    60
ccg                                                                  63

<210> SEQ ID NO 13
<211> LENGTH: 242
<212> TYPE: PRT
<213> ORGANISM: Artificial Sequence
<220> FEATURE:
<223> OTHER INFORMATION: synthetic
```

<400> SEQUENCE: 13

Met Gln Val Gln Leu Gln Gln Ser Gly Pro Glu Leu Lys Lys Pro Gly
1               5                   10                  15
Glu Thr Val Lys Ile Ser Cys Lys Ala Ser Gly Tyr Pro Phe Thr Asn
            20                  25                  30
Tyr Gly Met Asn Trp Val Lys Gln Ala Pro Gly Gln Gly Leu Lys Trp
        35                  40                  45
Met Gly Trp Ile Asn Thr Ser Thr Gly Glu Ser Thr Phe Ala Asp Asp
    50                  55                  60
Phe Lys Gly Arg Phe Asp Phe Ser Leu Glu Thr Ser Ala Asn Thr Ala
65                  70                  75                  80
Tyr Leu Gln Ile Asn Asn Leu Lys Ser Glu Asp Ser Ala Thr Tyr Phe
                85                  90                  95
Cys Ala Arg Trp Glu Val Tyr His Gly Tyr Val Pro Tyr Trp Gly Gln
            100                 105                 110
Gly Thr Thr Val Thr Val Ser Ser Gly Gly Gly Gly Ser Gly Gly Gly
        115                 120                 125
Gly Ser Gly Gly Gly Gly Ser Asp Ile Gln Leu Thr Gln Ser His Lys
    130                 135                 140
Phe Leu Ser Thr Ser Val Gly Asp Arg Val Ser Ile Thr Cys Lys Ala
145                 150                 155                 160
Ser Gln Asp Val Tyr Asn Ala Val Ala Trp Tyr Gln Gln Lys Pro Gly
                165                 170                 175
Gln Ser Pro Lys Leu Leu Ile Tyr Ser Ala Ser Ser Arg Tyr Thr Gly
            180                 185                 190
Val Pro Ser Arg Phe Thr Gly Ser Gly Ser Gly Pro Asp Phe Thr Phe
        195                 200                 205
Thr Ile Ser Ser Val Gln Ala Glu Asp Leu Ala Val Tyr Phe Cys Gln
    210                 215                 220
Gln His Phe Arg Thr Pro Phe Thr Phe Gly Ser Gly Thr Lys Leu Glu
225                 230                 235                 240
Ile Lys

<210> SEQ ID NO 14
<211> LENGTH: 726
<212> TYPE: DNA
<213> ORGANISM: Artificial Sequence
<220> FEATURE:
<223> OTHER INFORMATION: synthetic

<400> SEQUENCE: 14
atgcaggtac aactgcagca gtcaggacct gaactgaaga agcctggaga gacagtcaag      60
atctcctgca aggcctctgg gtatcctttc acaaactatg gaatgaactg ggtgaagcag     120
gctccaggac agggtttaaa gtggatgggc tggattaaca cctccactgg agagtcaaca     180
tttgctgatg acttcaaggg acggtttgac ttctctttgg aaacctctgc caacactgcc     240
tatttgcaga tcaacaacct caaaagtgaa gactcggcta catatttctg tgcaagatgg     300
gaggtttacc acggctacgt tccttactgg ggccaaggga ccacggtcac cgtttcctct     360
ggcggtggcg gttctggtgg cggtggctcc ggcggtggcg gttctgacat ccagctgacc     420
cagtctcaca aattcctgtc cacttcagta ggagacaggg tcagcatcac ctgcaaggcc     480
agtcaggatg tgtataatgc tgttgcctgg tatcaacaga aaccaggaca atctcctaaa     540
cttctgattt actcggcatc ctcccggtac actggagtcc cttctcgctt cactggcagt     600

-continued

```
ggctctgggc cggatttcac tttcaccatc agcagtgtgc aggctgaaga cctggcagtt    660
tatttctgtc agcaacattt tcgtactcca ttcacgttcg gctcggggac aaaattggag    720
atcaaa                                                                726
```

<210> SEQ ID NO 15
<211> LENGTH: 108
<212> TYPE: PRT
<213> ORGANISM: Artificial Sequence
<220> FEATURE:
<223> OTHER INFORMATION: synthetic

<400> SEQUENCE: 15

```
Lys Ile Glu Val Met Tyr Pro Pro Tyr Leu Asp Asn Glu Lys Ser
1               5                   10                  15

Asn Gly Thr Ile Ile His Val Lys Gly Lys His Leu Cys Pro Ser Pro
            20                  25                  30

Leu Phe Pro Gly Pro Ser Lys Pro Phe Trp Val Leu Val Val Val Gly
        35                  40                  45

Gly Val Leu Ala Cys Tyr Ser Leu Leu Val Thr Val Ala Phe Ile Ile
    50                  55                  60

Phe Trp Val Arg Ser Lys Arg Ser Arg Leu Leu His Ser Asp Tyr Met
65                  70                  75                  80

Asn Met Thr Pro Arg Arg Pro Gly Pro Thr Arg Lys His Tyr Gln Pro
                85                  90                  95

Tyr Ala Pro Pro Arg Asp Phe Ala Ala Tyr Arg Ser
            100                 105
```

<210> SEQ ID NO 16
<211> LENGTH: 324
<212> TYPE: DNA
<213> ORGANISM: Artificial Sequence
<220> FEATURE:
<223> OTHER INFORMATION: synthetic

<400> SEQUENCE: 16

```
aaaattgaag ttatgtatcc tcctccttac ctagacaatg agaagagcaa tggaaccatt     60
atccatgtga aagggaaaca cctttgtcca agtcccctat tccccggacc ttctaagccc    120
ttttgggtgc tggtggtggt tggtggagtc ctggcttgct atagcttgct agtaacagtg    180
gcctttatta ttttctgggt gaggagtaag aggagcaggc tcctgcacag tgactacatg    240
aacatgactc cccgccgccc cgggcccacc cgcaagcatt accagcccta tgccccacca    300
cgcgacttcg cagcctatcg ctcc                                            324
```

<210> SEQ ID NO 17
<211> LENGTH: 104
<212> TYPE: PRT
<213> ORGANISM: Artificial Sequence
<220> FEATURE:
<223> OTHER INFORMATION: synthetic

<400> SEQUENCE: 17

```
Ala Pro Ala Tyr Gln Gln Gly Gln Asn Gln Leu Tyr Asn Glu Leu Asn
1               5                   10                  15

Leu Gly Arg Arg Glu Glu Tyr Asp Val Leu Asp Lys Arg Gly Arg
            20                  25                  30

Asp Pro Glu Met Gly Gly Lys Pro Gln Arg Arg Lys Asn Pro Gln Glu
        35                  40                  45

Gly Leu Tyr Asn Glu Leu Gln Lys Asp Lys Met Ala Glu Ala Tyr Ser
```

```
                50                  55                  60
Glu Ile Gly Met Lys Gly Glu Arg Arg Gly Lys Gly His Asp Gly
 65                  70                  75                  80

Leu Tyr Gln Gly Leu Ser Thr Ala Thr Lys Asp Thr Tyr Asp Ala Leu
                 85                  90                  95

His Met Gln Ala Leu Pro Pro Arg
            100

<210> SEQ ID NO 18
<211> LENGTH: 315
<212> TYPE: DNA
<213> ORGANISM: Artificial Sequence
<220> FEATURE:
<223> OTHER INFORMATION: synthetic

<400> SEQUENCE: 18
gcccccgcgt accagcaggg ccagaaccag ctctataacg agctcaatct aggacgaaga     60
gaggagtacg atgttttgga caagagacgt ggccgggacc ctgagatggg gggaaagccg    120
cagagaagga agaaccctca ggaaggcctg tacaatgaac tgcagaaaga taagatggcg    180
gaggcctaca gtgagattgg gatgaaaggc gagcgccgga ggggcaaggg gcacgatggc    240
ctttaccagg gtctcagtac agccaccaag gacacctacg acgcccttca catgcaggcc    300
ctgccccctc gctaa                                                    315

<210> SEQ ID NO 19
<211> LENGTH: 26
<212> TYPE: PRT
<213> ORGANISM: Artificial Sequence
<220> FEATURE:
<223> OTHER INFORMATION: synthetic

<400> SEQUENCE: 19

Arg Arg Lys Arg Ser Gly Ser Gly Glu Gly Arg Gly Ser Leu Leu Thr
 1               5                  10                  15

Cys Gly Asp Val Glu Glu Asn Pro Gly Pro
            20                  25

<210> SEQ ID NO 20
<211> LENGTH: 78
<212> TYPE: DNA
<213> ORGANISM: Artificial Sequence
<220> FEATURE:
<223> OTHER INFORMATION: synthetic

<400> SEQUENCE: 20
agcggcagcg gcgagggaag aggaagcctg ctgacctgcg gcgatgtgga ggagaatccc     60
ggccccagga ggaagaga                                                  78

<210> SEQ ID NO 21
<211> LENGTH: 240
<212> TYPE: PRT
<213> ORGANISM: Artificial Sequence
<220> FEATURE:
<223> OTHER INFORMATION: synthetic

<400> SEQUENCE: 21

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Ser Thr Ala
            20                  25                  30
```

```
Val Ala Trp Tyr Gln Gln Lys Pro Gly Lys Ala Pro Lys Leu Leu Ile
         35                  40                  45
Tyr Ser Ala Ser Phe Leu Tyr Ser Gly Val Pro Ser Arg Phe Ser Gly
 50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Tyr Leu Tyr His Pro Ala
                 85                  90                  95
Thr Phe Gly Gln Gly Thr Lys Val Glu Ile Lys Gly Gly Gly Gly Ser
             100                 105                 110
Gly Gly Gly Gly Ser Gly Gly Gly Ser Glu Val Gln Leu Val Glu
         115                 120                 125
Ser Gly Gly Gly Leu Val Gln Pro Gly Gly Ser Leu Arg Leu Ser Cys
130                 135                 140
Ala Ala Ser Gly Phe Thr Phe Ser Asp Ser Trp Ile His Trp Val Arg
145                 150                 155                 160
Gln Ala Pro Gly Lys Gly Leu Glu Trp Val Ala Trp Ile Ser Pro Tyr
                 165                 170                 175
Gly Gly Ser Thr Tyr Tyr Ala Asp Ser Val Lys Gly Arg Phe Thr Ile
             180                 185                 190
Ser Ala Asp Thr Ser Lys Asn Thr Ala Tyr Leu Gln Met Asn Ser Leu
         195                 200                 205
Arg Ala Glu Asp Thr Ala Val Tyr Tyr Cys Ala Arg Arg His Trp Pro
     210                 215                 220
Gly Gly Phe Asp Tyr Trp Gly Gln Gly Thr Leu Val Thr Val Ser Ala
225                 230                 235                 240

<210> SEQ ID NO 22
<211> LENGTH: 720
<212> TYPE: DNA
<213> ORGANISM: Artificial Sequence
<220> FEATURE:
<223> OTHER INFORMATION: synthetic

<400> SEQUENCE: 22
gacatccaaa tgacccagag ccctagctcc ctgtccgcta gcgtgggcga cagggtgacc      60
atcacctgca gagccagcca ggacgtgagc accgccgtgg cctggtacca gcagaagccc     120
ggcaaggccc ccaagctgct gatctacagc gcctccttcc tgtactccgg cgtgccctcc     180
agatttagcg gcagcggcag cggcacagac ttcaccctca ccatcagctc cctgcagcct     240
gaggacttcg ccacatacta ctgccagcag tacctctacc accctgccac cttcggccaa     300
ggcaccaagg tggagatcaa gggcggcgga ggttctggcg gaggcggctc cggaggagga     360
ggcagcgaag tgcagctggt ggagagcgga ggaggactgg tgcagcctgg cggaagcctg     420
aggctgagct gtgctgccag cggcttcacc ttctccgact cctggattca ttgggtcagg     480
caggcccccg gaaaaggact ggagtgggtc gcctggatct cccttacgg cggcagcacc     540
tactacgccg acagcgtgaa gggcaggttc accatcagcg ccgataccag caagaacacc     600
gcctacctgc agatgaactc cctgagggct gaggacaccg ccgtgtacta ctgcgccagg     660
aggcactggc ctggcggatt cgactactgg ggccagggca ccctggtgac cgtgtccgcc     720

<210> SEQ ID NO 23
<211> LENGTH: 91
<212> TYPE: PRT
<213> ORGANISM: Artificial Sequence
<220> FEATURE:
```

<223> OTHER INFORMATION: synthetic

<400> SEQUENCE: 23

Ala Ala Ala Phe Val Pro Val Phe Leu Pro Ala Lys Pro Thr Thr Thr
1               5                   10                  15
Pro Ala Pro Arg Pro Pro Thr Pro Ala Pro Thr Ile Ala Ser Gln Pro
            20                  25                  30
Leu Ser Leu Arg Pro Glu Ala Cys Arg Pro Ala Ala Gly Gly Ala Val
        35                  40                  45
His Thr Arg Gly Leu Asp Phe Ala Cys Asp Ile Tyr Ile Trp Ala Pro
    50                  55                  60
Leu Ala Gly Thr Cys Gly Val Leu Leu Leu Ser Leu Val Ile Thr Leu
65                  70                  75                  80
Tyr Cys Asn His Arg Asn Arg Phe Ser Val Val
                85                  90

<210> SEQ ID NO 24
<211> LENGTH: 273
<212> TYPE: DNA
<213> ORGANISM: Artificial Sequence
<220> FEATURE:
<223> OTHER INFORMATION: synthetic

<400> SEQUENCE: 24
gcggccgcat tcgtgccggt cttcctgcca gcgaagccca ccacgacgcc agcgccgcga      60
ccaccaacac cggcgcccac catcgcgtcg cagcccctgt ccctgcgccc agaggcgtgc     120
cggccagcgg cgggggggcgc agtgcacacg aggggctgg acttcgcctg tgatatctac     180
atctgggcgc ccttggccgg gacttgtggg gtccttctcc tgtcactggt tatcacccttt    240 tactgcaacc acaggaaccg tttctctgtt gtt                                  273

<210> SEQ ID NO 25
<211> LENGTH: 42
<212> TYPE: PRT
<213> ORGANISM: Artificial Sequence
<220> FEATURE:
<223> OTHER INFORMATION: synthetic

<400> SEQUENCE: 25

Lys Arg Gly Arg Lys Lys Leu Leu Tyr Ile Phe Lys Gln Pro Phe Met
1               5                   10                  15
Arg Pro Val Gln Thr Thr Gln Glu Glu Asp Gly Cys Ser Cys Arg Phe
            20                  25                  30
Pro Glu Glu Glu Glu Gly Gly Cys Glu Leu
        35                  40

<210> SEQ ID NO 26
<211> LENGTH: 126
<212> TYPE: DNA
<213> ORGANISM: Artificial Sequence
<220> FEATURE:
<223> OTHER INFORMATION: synthetic

<400> SEQUENCE: 26
aaacggggca gaaagaaact cctgtatata ttcaaacaac catttatgag accagtacaa      60
actactcaag aggaagatgg ctgtagctgc cgatttccag aagaagaaga aggaggatgt     120
gaactg                                                                126